United States Patent
Hammiche et al.

(10) Patent No.: US 6,491,425 B1
(45) Date of Patent: *Dec. 10, 2002

(54) METHOD AND APPARATUS FOR PERFORMING LOCALIZED THERMAL ANALYSIS AND SUB-SURFACE IMAGING BY SCANNING THERMAL MICROSCOPY

(75) Inventors: Azzedine Hammiche, Lancaster; Hubert Murray Montagu-Pollock, Carnforth; Michael Reading, London; Mo Song, Lancaster, all of (GB)

(73) Assignee: TA Instruments, Inc., New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/584,396

(22) Filed: Jun. 1, 2000

Related U.S. Application Data

(63) Continuation of application No. 08/837,547, filed on Apr. 21, 1997, now Pat. No. 6,095,679.
(60) Provisional application No. 60/015,894, filed on Apr. 22, 1996.

(51) Int. Cl.[7] ............................................... G01H 25/20
(52) U.S. Cl. ............................................. 374/43; 374/10
(58) Field of Search .............................. 374/5, 10, 11, 374/31, 43, 44, 137, 167; 250/234

(56) References Cited

U.S. PATENT DOCUMENTS

| | | | | |
|---|---|---|---|---|
| 4,122,719 A | * | 10/1978 | Carlson et al. | 374/167 |
| 4,636,088 A | * | 1/1987 | Rosencwaig et al. | 374/5 |
| 5,067,820 A | * | 11/1991 | Donahue et al. | 374/31 |
| 5,224,775 A | * | 7/1993 | Reading et al. | 374/11 |
| 5,248,199 A | * | 9/1993 | Reading | 374/11 |
| 5,441,343 A | * | 8/1995 | Pylkki et al. | 374/137 |
| 5,535,614 A | * | 7/1996 | Okamoto et al. | 374/44 |
| 5,548,113 A | * | 8/1996 | Goldberg et al. | 250/234 |
| 5,549,387 A | * | 8/1996 | Schawe et al. | 374/31 |
| 5,711,604 A | * | 1/1998 | Nakamura | 374/44 |
| 5,788,373 A | * | 8/1998 | Huetter et al. | 374/43 |
| 5,806,979 A | * | 9/1998 | Gschneider, Jr. et al. | 374/43 |
| 5,813,763 A | * | 9/1998 | Plotnikov et al. | 374/412 |

\* cited by examiner

*Primary Examiner*—Peter S. Wong
*Assistant Examiner*—Pia Tibbits
(74) *Attorney, Agent, or Firm*—Shaw Pittman LLP

(57) ABSTRACT

A platinum/Rhodium resistance thermal probe is used as an active device which acts both as a highly localized heat source and as a detector to perform localized differential calorimetry, by thermally inducing and detecting events such as glass transitions, meltings, recystallizations and thermal decomposition within volumes of material estimated at a few $\mu m^3$. Furthermore, the probe is used to image variations in thermal conductivity and diffusivity, to perform depth profiling and sub-surface imaging. The maximum depth of the sample that is imaged is controlled by generating and detecting evanescent temperature waves in the sample.

27 Claims, 25 Drawing Sheets

METHOD AND APPARATUS FOR PERFORMING LOCALIZED THERMAL ANALYSIS AND SUB-SURFACE IMAGING BY SCANNING THERMAL MICROSCOPY

The present application is a continuation U.S. application Ser. No. 08/837,547, filed Apr. 21, 1997 (now U.S. Pat. No. 6,095,679), which claims the benefit of U.S. Provisional Application No. 60/015,894, filed on Apr. 22, 1996, both of which are hereby incorporated by reference herein in their entireties.

BACKGROUND

1. Field of the Invention

The present invention relates to determining thermal properties of materials using a miniaturized resistive thermal probe. More particularly, the present invention relates to performing localized thermal analysis experiments whereby calorimetric information is obtained from a volume of materials on the order of a few cubic microns, whereas in conventional bulk calorimetry data is obtained from volumes of material on the order of a few cubic millimeters. The present invention also relates to modulating the temperature of a thermal probe to generate evanescent thermal waves in a material to thereby generate sub-surface images.

2. Background of the Invention

Several methods for the non-destructive characterization of solids make use of thermal excitation. Any local disruption of the structure that results in a change in density, specific heat, or thermal conductivity may be detected by some type of thermal probe—often with higher sensitivity than by the use of optical, X-ray, or electron-microscope techniques. Many of these techniques use an intensity-modulated energy source to excite a sample. That is, the intensity of the energy source used to excite the sample is made to vary with time. Induced scattered evanescent thermal waves are then detected by, for example, monitoring the surface temperature of the sample. When a scanning mechanism is also incorporated, it is then possible to achieve spatial thermal mapping. Subsurface imaging can be performed within the depth of penetration of the thermal wave.

Most conventional methods of thermal imaging employ an energy beam that emerges from a small source and spreads out according to the rules of diffraction. The extent of this spreading is normally governed by the wavelength associated with the energy flux. However, if the sample is within the "near-field" region, i.e., significantly less than one wavelength away from the source, then a greatly reduced beam diameter can be achieved. In this case, the beam diameter is not much larger than the size of the source itself.

This principle is applied in Scanning Probe Microscopy whereby a sharp probe is brought in close proximity to the surface of a sample. Some probe/sample interaction takes place. This interaction is monitored as the probe is scanned over the surface. An image contrast is then computer-generated. The image contrast represents variations of some property (e.g., physical, mechanical, chemical) of the sample across the scanned area. One such scanning probe microscope is the Atomic Force Microscope (AFM). In conventional AFM, the height of a probe above the surface being scanned is controlled by a feedback system, that keeps the force between the probe and the surface of the sample constant. The probe height is monitored, and provides the data that is used to create image contrast which represents the topography of the scanned area.

Near-field thermal imaging is described by C. C. Williams and H. K. Wickramasinghe in *Photoacoustic and Photothermal Phenomena*, P. Hess and J. Peltzl (eds.), p. 364 (1988). In their device, the probe is a specially made coaxial tip that forms a fine thermocouple junction. This probe provides a spatial resolution on the order of tens of millimeters. The sample is either heated using a laser or the probe, or the sample is heated electrically. The feedback system maintains the probe temperature constant (instead of maintaining the force constant), by varying the probe height as necessary.

In "Thermal Imaging Using the Atomic Force Microscope," *Appl. Phys. Lett.*, vol. 62, pp. 2501–3 (1993), Majumdar, et al. describe a technique for thermal imaging that uses a simpler design of thermocouple tip, than that disclosed by Williams and Wickramasinghe. Majundar, et al. implemented standard atomic force microscopy feedback to maintain tip/sample contact. R. B. Dinwiddie, R. J. Pylkki and P. E. West "Thermal Conductivity Contrast Imaging with a Scanning Thermal Microscope," *Thermal Conductivity* 22, T. W. Tong (ed.) (1994), describe the use of a probe in the form of a tiny platinum resistance thermometer. U.S. Pat. No. 5,441,343 to Pylkki et al., which is incorporated herein by reference, discloses the thermal sensing probe for use with a scanning probe microscope, in which the contact force of the probe is maintained at a constant level as the probe is scanned across the surface of the sample.

In those studies, the samples were generally probed at a constant (ac or dc) amplitude of either surface temperature or heat flow. Thus changes in the thermal properties of materials, such as heat capacity or thermal conductivity, were not investigated. This is because the temperature of the sample was not raised by a sufficient amount for a change in the sample's thermal properties to be detected.

Bulk thermal analysis techniques have been developed to study such changes in the thermal properties of materials. Modulated temperature differential scanning microscopy (MDSC) and spatially-resolved modulated differential scanning calorimetry (SR-MDSC) are described in U.S. Pat. No. 5,224,775 ('775 patent) and U.S. Pat. No. 5,248,199, respectively, which are both incorporated herein by reference. A conventional heat flux differential scanning calorimeter (DSC) measures the heat flow into and out of a sample with respect to a reference. Both sample and reference are usually subjected to a linear temperature/time ramp. In one implementation of MDSC, a sinusoidal modulation is superimposed on the underlying heating ramp to generate a corresponding sinusoidal response in the heat flow signal. This results in two measurements of heat capacity, an underlying linear long-period measurement due to the underlying heating ramp and a higher-frequency cyclic measurement due to the superimposed sinusoidal modulation. For many systems the cyclic measurement "sees" only the reversible heat capacity associated with molecular vibrations, e.g., glass transitions, whereas the underlying measurement also sees endotherms and exotherms associated with kinetically-controlled events such as recrystallization cure reactions or the loss of volatile materials.

SUMMARY OF THE INVENTION

The present invention is a new analytical technique which makes calorimetric measurements on a localized scale. Data obtained from the measurement can be used to generate contrast in our image of the thermal properties of the sample on a localized scale. In addition, by subjecting the sample to an oscillating program, images of the sample at a depth below the surface can be made. The depth corresponds to the frequency of the applied oscillatory temperature.

The present invention applies modulated temperature differential scanning calorimetry, as described in U.S. Pat.

No. 5,224,755 to Reading, et al. ('775 patent), which has been conventionally used to perform bulk thermal analysis experiments of a sample material, to microscopic thermal analysis of a sample material using two highly miniaturized resistive probes, developed by the Topometrix Corporation (U.S. Pat. No. 5,441,343 to Pylkki et al. ('343 patent)), in a differential configuration. A sample probe attached to a Scanning Probe Microscope is positioned at a desired location on the surface within the field of view. Localized calorimetry is then performed at that position by inducing and detecting localized phase transitions. This is achieved by ramping the temperature of the probe by passing an electrical current through the probe. A small temperature oscillation is superimposed to that temperature ramp by adding a modulated component to current the probe current. By scanning over the surface of the sample, contrast can be developed corresponding to particular locations on the sample to create an image of the thermal properties of the sample at particular locations.

A second embodiment of the present invention allows for sub-surface imaging thermal microscopy to be performed by modulating the temperature of the probe. This is done by passing a modulated current through it, thus generating thermal waves within the sample. The depth of penetration of these waves is frequency dependent, such that the thermal properties of a sample can be probed as a function of depth below the surface.

The probe, developed by the Topometrix Corporation, is an elongated loop of Wollaston wire, shaped in the form of a canteliver whose end forms the resistive element. The resistance of that element varies with temperature. Conversely, its temperature can be set by passing a current of appropriate value through it. A mirror is attached across the loop allowing for the contact force of the element on the sample to be held constant, as in conventional atomic force microscopy, while the probe is scanned across the surface of the sample.

In the two embodiments of the present invention, the probe is used as a highly localized heat source by passing a current through it. The temperature of the probe is either constant, or is variable as a function of time. As the probe is brought close to the surface of a sample, heat will flow from the probe to the sample. The amount of heat flowing will vary according to various properties of the sample at the location under the probe. This varying heat flow causes the temperature of the resistive element to change, thereby changing its resistance. A feedback circuit is preferably used to sense the change in the probe resistance (and therefore its temperature) and increase the amount of current flowing through the probe to bring it back to its original resistance value (and therefore to its set temperature). A differential signal is then monitored, either directly or through a lock-in amplifier. The differential signal is used to either (1) produce localized analysis plots of amplitude and phase data versus temperature that provide calorimetric information at a specific position on the sample, or (2) construct an image whose contrasts represent variations in thermal conductivity and/or diffusivity across a scanned area. In the second case, the time-varying current through the resistive elements generates thermal waves in the sample. The modulation frequency of the time-varying current is functionally related to the depth below the surface of the sample at which an image of the sample is desired. A sub-surface image is thus generated. The depth of material below the sample surface that is contributing to the image can be controlled by suitably choosing the temperature modulation frequency. As described in Almond, et al., "Photothermal Science and Techniques," page 15, Chapman and Hall (London 1996), which is hereby incorporated by reference in its entirety, the penetration depth is proportional to the square root of the thermal diffusivity of the sample divided by the frequency of the applied temperature wave.

OBJECTS OF THE INVENTION

A first object of the present invention is to provide localized differential thermal analysis at the micron level, such that events such as glass transitions and meltings can be induced in a highly spatially localized manner and identified.

A second object of the present invention is to use scanning thermal microscopy to obtain sub-surface images of solids, in which the image contrast is due to variations in thermal diffusivity within a given controllable depth.

Another object of the present invention is to use a highly miniaturized resistive thermal probe as a highly localized source of heat, such that it can be used to produce highly localized phase transitions at the surface of samples.

Another object of the invention is to use modulated differential scanning calorimetric signals to produce a high-frequency temperature modulation in a probe used for sensing the thermal properties of materials at different depths below the surface.

Another object of the present invention is to provide an apparatus which can, for a sample containing different regions subject to either reversible or irreversible changes with temperature, produce thermal images showing contrast based upon the reversing and nonreversing nature of the heat flow, respectively.

These and other objects of the present invention are described in greater detail in the detailed description of the invention, the appended drawings and the attached claims.

DESCRIPTION OF THE DRAWINGS

FIG. 17A: nylon 6 (210–220° C.) (the inset shows a probe current versus temperature characteristic used to achieve linearization for all the data presented in this example).

FIG. 17B: nylon 6/6 (240–265° C.).

FIG. 17C nylon 6/10 (190–220° C.).

FIG. 17D polyethylene (130–140° C.).

FIG. 17E: polyvinylidene fluoride (155–185° C.).

FIG. 18A: polystyrene (90–110° C.).

FIG. 18B: poly(ethyl methacrylate) (60–90° C.).

DETAILED DESCRIPTION OF THE INVENTION

The scanning probe system used in the preferred embodiment of the present invention is the Explorer scanning probe microscope manufactured by the Topometrix Corporation, located in Santa Clara, Calif. Preferably, the system is operated as a constant force microscope. When operated as a force microscope, the Topometrix instrument uses a laser, together with a four-quadrant photodiode as the detection system for cantilever deflection. The scanner, probe and detection system form a self-contained system mounted independently of the sample. The sample is therefore free to be mounted on an appropriate stage (a heating stage for example).

Figure 1:
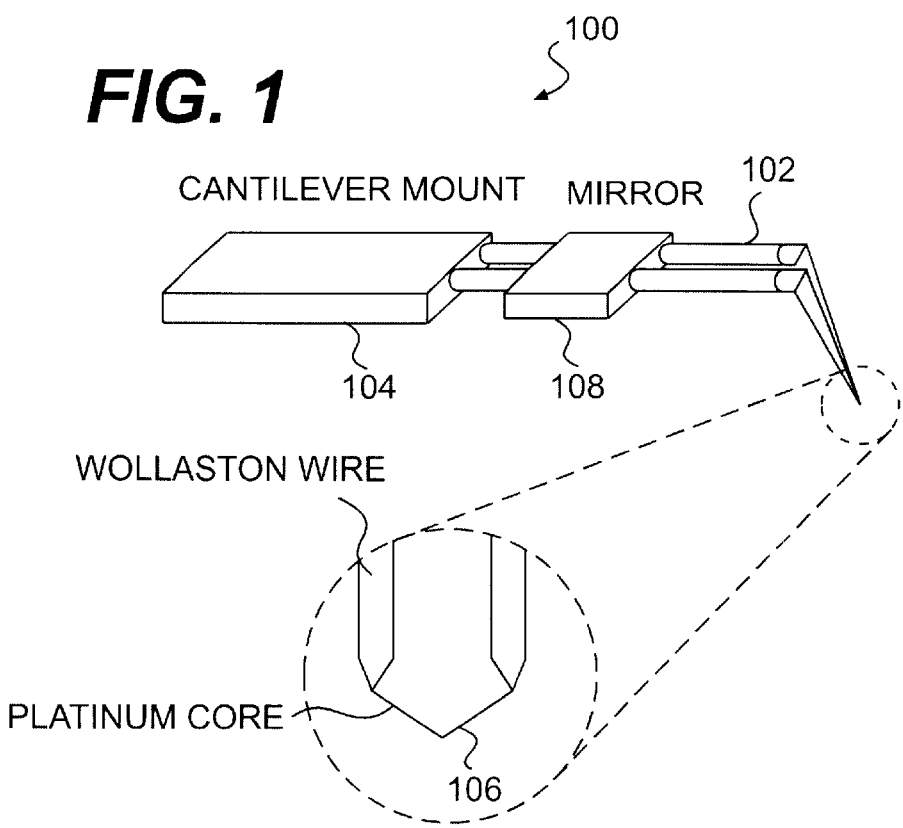
FIG. 1 is a schematic diagram of the cantilevered thermal resistance probe.

FIG. 1 illustrates schematically a resistive thermal probe 100 for use in a preferred embodiment of the present invention. The probe 100 comprises a cantilever 102 mounted to a cantilever mount 104. The arms of the cantilever are made of Wollaston process wire having silver wire that is preferably 75 $\mu$m in diameter. The silver wire preferably contains a platinum/10% rhodium core. The platinum/rhodium core is preferably 5 $\mu$m in diameter. The arms of the cantilever form a loop 106 at one end of the probe 100. Where the loop 106 is formed, the silver is etched away, thereby exposing the platinum/10% rhodium core. The length of the exposed core is preferably 150–200 $\mu$m in length. The loop 106 is the resistive heating source of the probe 100. As shown in FIG. 1, the cantilever 102 of the probe 100 is bent to a suitable shape, i.e., has as sharp a bend as possible. The sharp bend yields a very small area of contact with the sample. The small area of contact with the sample allows for precise heating of a particular location on the sample. Such a probe 100 is commercially available from the Topometrix Corporation.

The probe 100 is attached to a scanning probe microscope via the cantilever mount 104. Part of the structure acts as a cantilever 102 onto which a mirror 108 is cemented for the purpose of laser beam deflection in order to achieve force control. The mirror 108 reflects a laser beam to a four-quadrant photodiode (not shown). The laser/mirror/photodiode system is used to sense the cantilever deflection, and thus to provide feedback to enable the probe 100 to be scanned at constant force. The probe 100 is held magnetically in place on the scanner in a well-known manner. An epoxy bead (not shown) is added near the end of the cantilever to reduce the risk of breaking the filament. Such a scanning probe system is the Explorer scanning probe microscope produced by Topometrix Corporation.

The resistive thermal probe 100 can be used as a highly localized heat source as well as a detector. When heated by the passage of an electric current through the resistive portion 106 of the probe 100, its contact with the sample acts as a point-like heat source. Therefore, no other means of sample heating, such as a laser, is required. The probe 100 is attached to a scanning mechanism, and is controlled to obtain thermal image contrast that corresponds to variations in either thermal conductivity (using DC imaging) or thermal diffusivity (using AC imaging).

A conventional method for operating the probe is in the constant temperature, self-heating mode. The thermal element is used as a resistive heater, as well as functioning as a temperature sensor. As illustrated schematically in FIG. 2, the probe 100 forms one of the legs of a Wheatstone bridge 204. The remaining legs of the wheatstone bridge 204 are formed by resistors $R_1$ and $R_2$, and a resistor $R_C$. Resistors $R_1$ and $R_2$ are chosen to have constant values. The resistor $R_C$ is chosen to provide the set point for the bridge voltage as described below. The resistor $R_L$ accounts for the resistance of the probe's 100's probe leads.

The Wheatstone bridge circuit 204 uses a feedback loop 205 to adjust a bridge voltage $V_b$ as necessary to keep the bridge 204 balanced. By maintaining the balance of the bridge 204, the temperature of the probe is kept constant. The feedback loop 205 generally comprises a difference amplifier 206 and a feedback circuit 212. The difference amplifier 206 has a first input 207, coupled to a junction 208 and a second input 209 coupled to a junction 210. The second input 209 is the inverted input of the difference amplifier 206. The difference amplifier determines the voltage difference across the junctions 208 and 210. The voltage difference is input to the feedback circuit 212 to adjust the bridge voltage $V_b$ as required. The amount of adjustment required to maintain the bridge balance is used to develop contrast in an image. For example, the spot intensity on a cathode ray tube (CRT) screen can be made to be proportional to the bridge adjustment voltage.

As the probe 100 contacts the sample surface 216, heat flows from the probe 100 to the sample. In the absence of temperature feedback, this flow of heat reduces the probe temperature, decreasing its resistance and causing the bridge balance to shift. The feedback loop 205 senses this shift through difference amplifier 206 and increases the voltage, $V_b$, applied to the bridge. This in turn increases the resistive heating of the probe 100, returning its resistance to the set point. The set point is the probe resistance that corresponds to a constant desired operating temperature, and is set by appropriately choosing the value of $R_c$. The probe 100 is scanned at constant force. Variations in the heat flow out of the probe 100 are measured by monitoring the bridge voltage $V_b$ required to maintain the probe's 100's resistance such that it produces the content desired operating temperature. The bridge voltage signal $V_b$ is then used to create contrast in the thermal image.

Figure 3A:
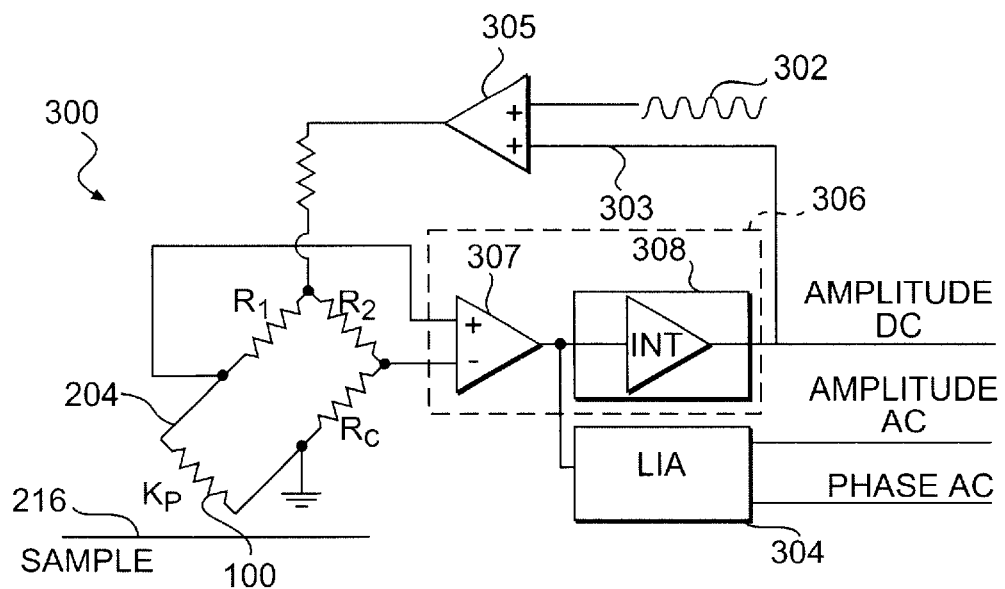
FIGS. 3A–3C are schematic diagrams of alternative probe control and sensing circuits.

Referring to FIG. 3A, a schematic diagram illustrating a first preferred embodiment of the present invention is presented. The first embodiment both maintains a constant underlying temperature when scanning the surface of a sample and generates thermal waves into the sample. It does so by incorporating control circuitry 300 that adds an oscillating voltage signal 302 to an underlying DC voltage signal 303 to cause the temperature of the region of the sample 216 in contact with the probe to oscillate about a fixed temperature. The fixed temperature is set by the value of resistor $R_c$ and maintained by operation of the feedback circuit 306.

A summing circuit 305 is used to sum the oscillating voltage signal 302 with the voltage set by the feedback circuit 306. The voltage set by the feedback circuit 306 is the voltage that is required to maintain the probe at a constant temperature (set by $R_c$). The addition of the oscillating voltage signal 302 generates a thermal wave in the sample 216. The bridge 204 imbalance caused by the heat flow out of the probe 100 to the sample is monitored using a lock-in amplifier (LIA) 304. LIAs, such as LIA 304, are well-known devices that are used for coherent detection and recovery of modulated signals having a low signal-to-noise (SNR) ratio, i.e., that are buried in noise. Thus, the LIA 304 determines the amplitude and phase of the heat flow due to the oscillating voltage signal 302. This information is subsequently used to generate contrast in an image as described further below. The LIA computes the amplitude and phase (relative to a reference) of the modulated signal of interest. In the preferred embodiment, the reference is the oscillating voltage 302. The LIA 304 of the present invention preferably has a frequency range from approximately 1 millihertz (mHz) to approximately 1 megahertz (MHz).

The feedback circuit 306 preferably includes a differential stage 307 and an integration stage 308. The differential stage 305 determines the error between the set point value and the value actually measured. The error is input to the integrator in stage 308. The integrator 308 attempts to force the error to zero. Variations in the AC signal due to the heat flow from the probe 100 to the sample 216 are used to generate contrast in an image which represents variations in thermal diffusivity at a given temperature (set by $R_c$) within the thermal wave diffusion length. This is accomplished by monitoring the amplitude and the phase of the ac signal, using the LIA 304.

Using the values of the generated dc amplitude, ac amplitude and/or ac phase signals, contrast is developed in an image of the sample. The image represents a depth of the sample determined by the frequency of the applied oscillating voltage 302. In the preferred embodiment, the value of the contrast is proportional to the value of the generated dc amplitude, ac amplitude, or ac phase signal used to generate the contrast.

Figure 3B:
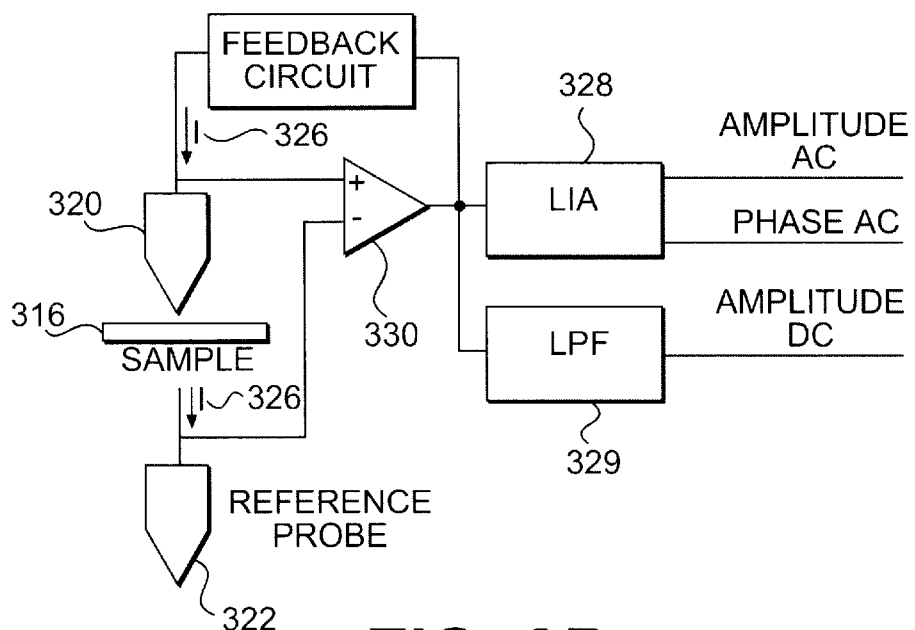
Figure 3C:
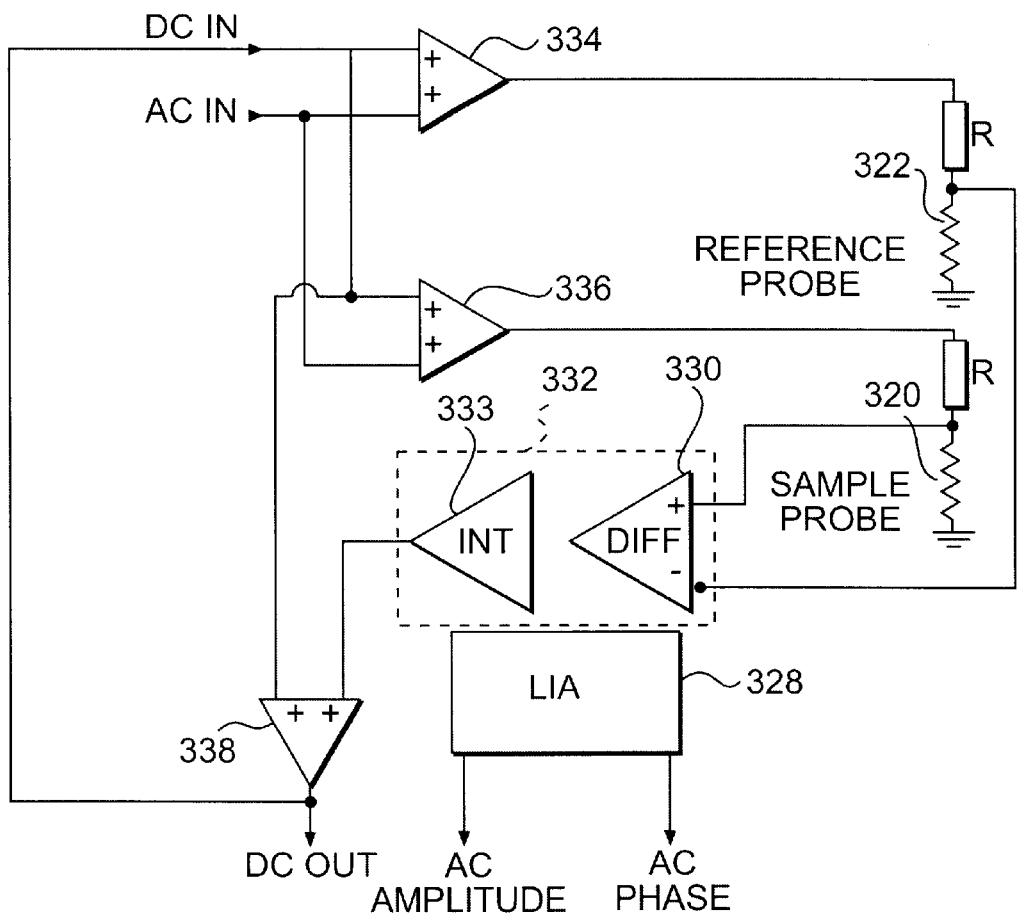

A second preferred embodiment of the present invention is illustrated schematically in FIGS. 3B and 3C. The second preferred embodiment incorporates two probes, a sample probe 320 and a reference probe 322, to perform localized thermal analysis at the surface of the sample 316. For example, localized MDSC experiments, such as those described in the '775 patent, can be performed at a location on the surface of the sample, rather than for the sample bulk as in conventional systems. In the preferred embodiment, both the sample probe 320 and the reference probe 322 are similar to the probe 100 described above.

Figure 3D:
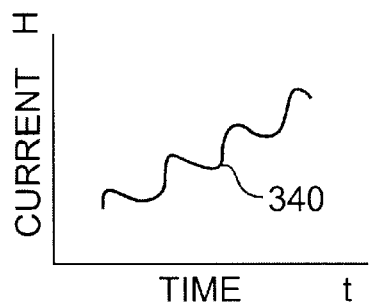

According to the preferred embodiment of the present invention, a particular location on the sample at which to perform a localized thermal analysis is selected by first obtaining a thermal image of the sample. The thermal image can be obtained by a technique according to the first embodiment of the present invention or any other technique. Using the thermal image, the particular location is selected. One method for selecting the particular location is to use a pointing and selection device, such as a computer mouse, to select the particular location by pointing to and clicking on a particular location in a representation of the thermal image that is displayed on a computer monitor. The sample probe 320 is then positioned at the particular location by the scanning probe microscope system. When the sample probe 320 is properly positioned at the particular location, a thermal analysis is performed by supplying the sample probe 320 with a current to produce a heating function according to a temperature program as described below, Equal currents (I) 326 are passed into the reference probe 320 and into the sample probe 322. An example of the currents 326 is illustrated graphically in FIG. 3D as current 340. As shown, the current 340 has a constant underlying heating rate on which a modulating signal is superimposed. In the preferred embodiment, the modulating signal is sinusoidal in character. However, as described in the '775 patent, the modulating signal can assume a variety of functions.

The current 340 can be generated in accordance with any desired temperature program. For example, temperature programs used in conventional bulk analyses can be used. In addition to the sinusoidal current described above for example, the current 340 can be created by choosing a repeating unit, and a number of repetitions for the repeating unit. Various parameters relating to the temperature program can be determined from the temperature program subsequent to its generation. For example, the underlying heating rate can be determined by averaging over a single period of the temperature program. Moreover, the frequency can be determined as the reciprocal of the period. In addition, the temperature as measured by the sample probe 320 can be used to calculate the underlying heating rate, and modulation amplitude and frequency as required. These parameters can be determined, or selected, by a computer or a user.

Referring back to FIG. 3B, the sample probe 320 is in mechanical contact with the surface of the sample 316 at a fixed location. The reference probe 322 is preferably not in contact with any sample. As described below with reference to FIG. 3C, each current 326 is the sum of an alternating current (ac) component and a direct current (dc) component. The ac component produces ac heating in the probes 320 and 322. To increase the sample temperature, the currents in the probes 320 and 322 are increased accordingly. Using the present invention therefore, a localized portion of The sample is exposed to a temperature that varies in an analogous manner to the current 340 illustrated in FIG. 3D.

The difference between the voltages across the probes is fed into a lock-in-amplifier 328. A differential amplifier 330 can be used to determine the difference. Three signals are derived using this configuration. First, a DC signal is obtained after low pass filtering through a low pass filter (LPF) 329. The DC signal contains information that is related to the underlying temperature of the equal currents 326. The two remaining signals are output by the LIA 328. The LIA 328 outputs one signal that is representative of the AC amplitude of the differential AC signal. The LIA 328 also outputs a signal that is representative of the phase of the AC differential signal. These signals can be plotted, displayed in real time, e.g., on a CRT display, such as a computer monitor, or an oscilloscope, and/or stored to a computer disk or any other storage device.

Using these signals, the temperature at which the sample undergoes a phase transition at the particular location analyzed can be determined. The phase transition is indicated by a sharp transition or peak in one or more of the three signals. The resulting amplitude and phase data can be displayed or plotted in a variety of ways. For example, plots of amplitude versus temperature and phase versus temperature can be made at specific location on the surface of the sample. In an alternative embodiment, layered plots of amplitude versus temperature and phase versus temperature can be made for locations taken at even intervals across the surface of the sample as the surface is scanned by the sample probe 320.

FIG. 3C is a more detailed schematic diagram of the circuitry used to perform localized MDSC. FIG. 3C shows an integral control feedback circuit 332. It includes an integrator 333 and a differential amplifier 330, which are used to maintain the DC temperature of the sample probe 320 at the value set by the reference probe 322. The feedback circuit 332 forces the difference between the voltage across the sample probe 320 to be equal to the voltage across the reference probe 322 by forcing the error between the voltages measured by the sample probe 320 and the reference probe 322 to zero. In addition, an alternating current (ac IN) is injected into the two probes to produce AC heating using the summing circuits 334 and 336.

The bandwidth of the feedback circuit 332 can be set higher to or lower than the frequency of the ac modulation. If set higher, the feedback circuit 332 responds to both the ac and dc components of the error signal. If set lower, the feedback circuit 332 only responds to the dc component of the error signal. This flexibility provides and additional parameter for conducting an experiment. Where the frequency is set depends on the given experiment. Considerations as to whether to use a higher or lower frequency include the sample material being studied and the localized phase transition through which the sample material is driven. Preferably, the bandwidth of the feedback circuit 332 is set to 1 kHz. Furthermore, the current used is preferably such that a temperature oscillation of about one degree amplitude is obtained. The differential voltage across the two probes is monitored by the differential amplifier 332. Three signals are recorded: the amplitude of the differential underlying signal (DC OUT), as measured by a summing circuit 338, and the phase (PHASE) and amplitude (AMP) of the dynamic signal, as measured by the lock-in amplifier 328. The DC OUT signal is fed back to the dc in input of the summing circuit 334. These three signals can be digitized and read into a computer, or displayed in real time, e.g., on a CRT display, such as a computer monitor, or an oscilloscope. As described above, various plots or displays of the data can be made using these signals.

As in any macroscopic differential scanning calorimeter measurement, the temperature ramp generally produces variations in the thermal conductivity and heat capacity of the sample, which may also undergo local phase changes. The apparatus of FIG. 3C uses local heating rather than a heating stage, so that these temperature-induced variations will themselves be subject to spatial variation according to where the sample probe is positioned. In turn, the heat flow out of the probe, and therefore the resistance and the voltage across the probe, vary according to where the sample probe is positioned. This is reflected in the variations of the amplitude and phase of the differential signals, as well as in the DC signal. The probed volume of material in the present invention is of the order of a few $\mu m^3$. The probed volume is the smallest volume that can be used to generate a useful localized MDSC scan. It can be used to map thermally activated near-surface processes such as glass transitions, melting, cure reactions, recrystallizations and degradations. Because the probes are used as heat sources as well as detectors, using a single probe would give a baseline which would tend to hide any variations in the signal indicative of phase changes between the applied temperature and the resulting measurement. An important feature of the differential arrangement is that by means of the feedback mechanism, the sample probe is maintained at the same temperature as the reference probe.

Mathematical Modeling and Simulation of Thermal Imaging in the Case of a Constant Temperature Mode of Operation A one-dimensional mathematical model which describes the probe-sample interaction has been developed in the simple case of constant temperature (DC) thermal imaging. DC imaging can be considered as the extreme case of AC imaging when the frequency is zero. This mathematical model illustrates the sub-surface imaging capability of the present invention.

Measurement of Heat Flow

Figure 2:
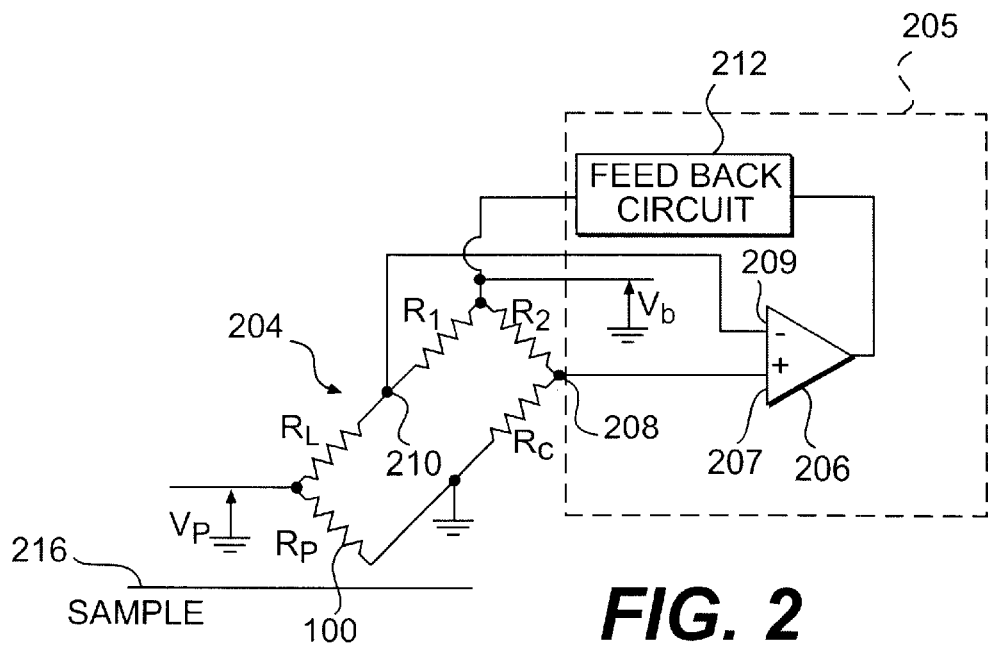
FIG. 2 is a circuit diagram of the probe control and sensing circuit.

The flow of heat in the sample can be related to the heat dissipated in the resistive element and therefore to the voltage applied to the bridge as follows:

The resistance $R_p$ of the probe (and therefore its temperature T) is set by selecting $R_c$ (see FIG. 2). This resistance can be expressed as:

$$R_p = R_c \frac{R_1}{R_2} - R_l = R_a[(T - T_a)\alpha + 1]$$

where $\alpha$ is the temperature coefficient of the resistance of the probe material, $T_a$ is the ambient temperature, $R_a$ is the resistance of the probe at ambient temperature and $R_l$ is the lead resistance.

When the probe is away from the sample, the energy dissipated in the probe to raise its temperature to the desired value T is then given by:

$$Q_{p0} = \frac{V_{p0}^2}{R_p}$$

where $V_{p0}$ is the voltage across the probe and is calculated from the bridge voltage $V_{b0}$ as:

$$V_{p0} = V_{b0} \frac{R_p}{R_p + R_l + R_1}$$

(Part of the electrical energy resistively dissipated in the probe will heat up a certain volume of surrounding air).

As the probe is lowered towards the sample heat will flow out, lowering the temperature and resistance of the probe, but the feedback circuit increases the energy dissipated in the probe and readjusts its temperature (and resistance) to the set value, as determined by $R_c$.

The heat dissipated in the probe is now:

$$Q_p = \frac{V_p^2}{R_p}$$

where the new voltage probe $V_p$ is calculated from the bridge feedback voltage V.

The electrical energy dissipated in the probe now also includes heat flowing into the sample. This outflow of heat can thus be measured and is given by:

Calculations—Basic One-Dimensional Heat Flow Model $$Q_f = Q_p - Q_{p0}$$

Figure 4:
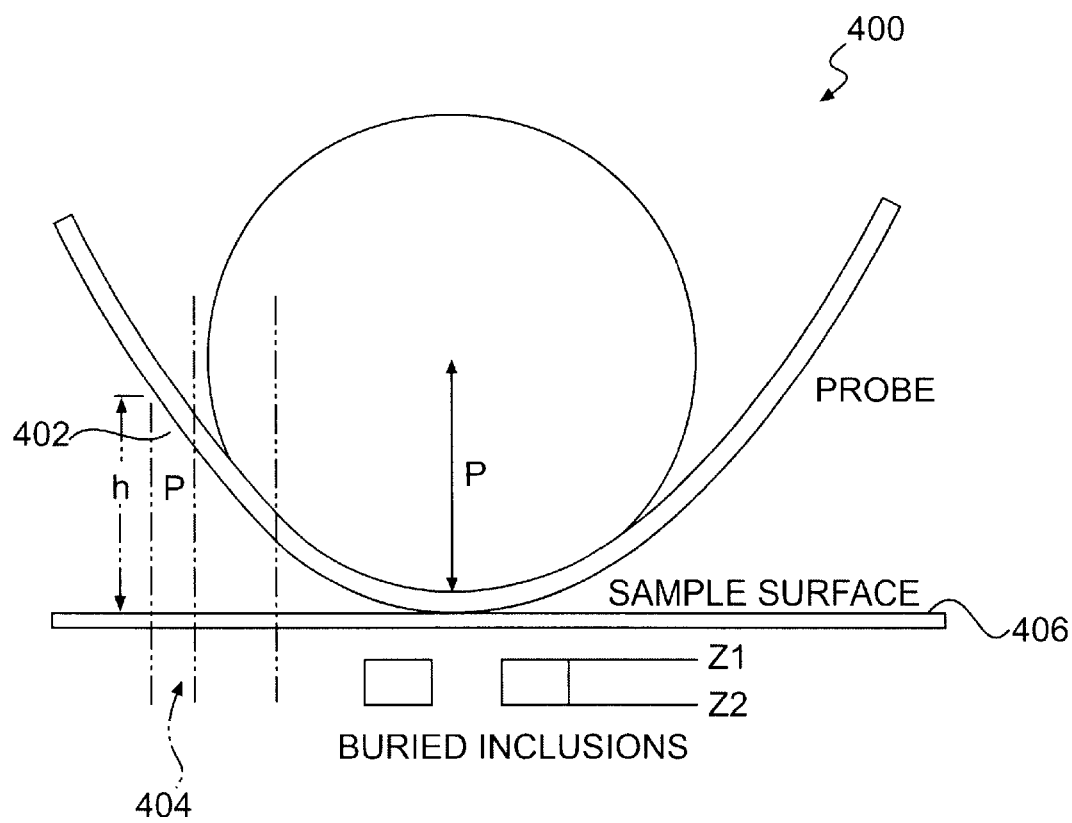
FIG. 4 is an illustration of the probe in relation to buried inclusions.
Figure 5:
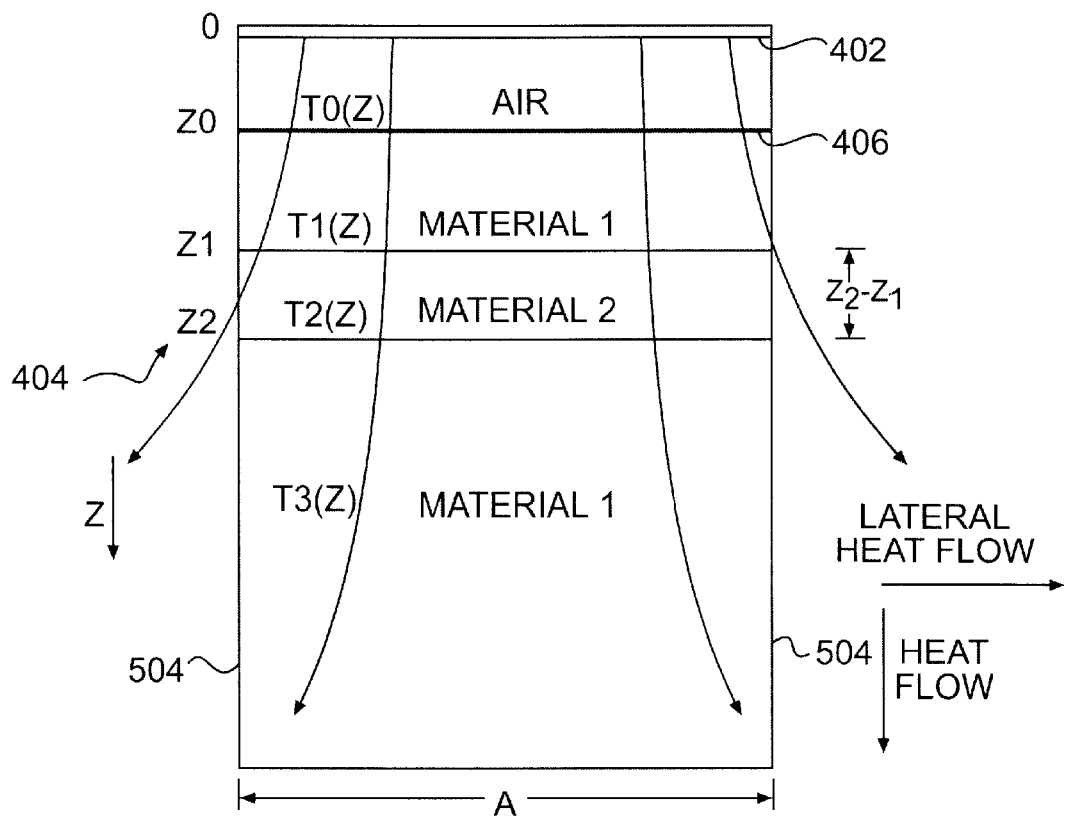
FIG. 5 is a detail of the semi-infinite volume element of FIG. 4.

The flow of heat in the sample is affected by several factors including the contact area of the probe, the temperature difference between probe and sample and the thermal conductivity of the sample. FIG. 4 is a schematic diagram depicting the probe 400 in contact with the surface of a sample 406. The probe is modeled as a series of elemental contiguous heat sources 402, each having the same projected area of cross-section A. For example, elemental heat source 402 is over volume element 404. The elemental heat sources are all at the same temperature, but are located at different heights above the surface of the sample 406. To simplify the heat flow calculation, the heat flow is assumed to be unidirectional along the z-direction into the sample. As illustrated in FIG. 5, this assumption is a major simplification to the heat flow. In reality, there is a lateral component 502 to the heat flow in each volume element. FIG. 5 depicts an expanded view of volume element 404. The effect of the lateral component of the heat flow 502 is accounted for by considering the walls of the element as not being thermally insulating. The loss at the walls is then modeled by including a loss coefficient E which represents heat loss through the walls of the element 504.

Consider an element of cross-section A extending through a layer of thickness $(z_2-z_1)$ (material 2) embedded at depth $z_1$ in a semi-infinite matrix (material 1). The thermal conductivities of material 1 and material 2 are $k_1$ and $k_2$, respectively. The corresponding part of the surface of the thermal probe 408, which is the heat source, is at a distance $z_o$ from the surface. Heat conduction into the sample is through a layer of air whose thermal conductivity is $k_o$. The loss coefficient $\epsilon$, which represents heat flow through the walls of the element, is assumed to be constant along the length of the element of volume.

In this one-dimensional approximation, the temperature profile in the heated element can be described by the following differential equation:

$$Ak_i \frac{d^2 T_i(z)}{dz^2} = p \epsilon T_i(z)$$

with i=0, 1, 2, 3. The general solution is:

$$T_i(z) = P_i e^{\mu_i z} + Q_i e^{-\mu_i z}$$

where $\mu_i = \sqrt{\frac{\epsilon p}{k_i A}}$ and where P and Q are constants. The solution to the problem is found using the following boundary conditions, which define temperature and heat flow continuity ($T_i$ is the temperature above ambient):

$$T_0(0) = T_0 \quad T_3(\infty) = 0$$

$$T_0(z_0) = T_1(z_0) \quad T_1(z_1) = T_2(z_1) \quad T_2(z_2) = T_3(z_2)$$

$$k_0 \frac{dT_0(z)}{dz}\bigg|_{z=z_0} = k_1 \frac{dT_1(z)}{dz}\bigg|_{z=z_0}$$

$$k_1 \frac{dT_1(z)}{dz}\bigg|_{z=z_1} = k_2 \frac{dT_2(z)}{dz}\bigg|_{z=z_1}$$

$$k_2 \frac{dT_2(z)}{dz}\bigg|_{z=z_2} = k_1 \frac{dT_3(z)}{dz}\bigg|_{z=z_2}$$

These equations enable the determination of the eight unknowns $P_i$, $Q_i$, and thus the determination of the temperature profiles $T_i(z)$. The theoretical value of heat flow $Q_{f\,elm}$ into the heated element is given by:

$$Q_{f\,elm} = -k_0 A \frac{dT_0(z)}{dz}\bigg|_{z=0}. \tag{1}$$

The value of the loss coefficient $\epsilon$ can be determined as follows. Heat flow from the probe into the sample was determined experimentally for various probe positions over homogeneous regions and over regions with buried inclusions of different sizes, e.g., 0.4 μm, 1.0 μm and 4.0 μm. The values of $\epsilon$ for each probe position are then calculated using these experimentally measured values of heat flow, the theoretical expression for the heat flow into the sample given above in equation (1), the assumed nominal values of burial depth and thickness of the inclusions, (whose thicknesses are assumed to be about one-third of the observed lateral size of the inclusions), and the values of the thermal conductivity for copper and for polystyrene shown in Table II below. The calculated values of $\epsilon$ determined at each probe position are then averaged to determine $\epsilon$ for use in subsequent calculations.

Using the calculated value of the loss coefficient $\epsilon$, the total heat flow is calculated by summing the elemental heat flows along the profile of the probe, out to where the air gap was 100 μm wide. The temperature of the probe was assumed to be constant along its length.

Figure 6:
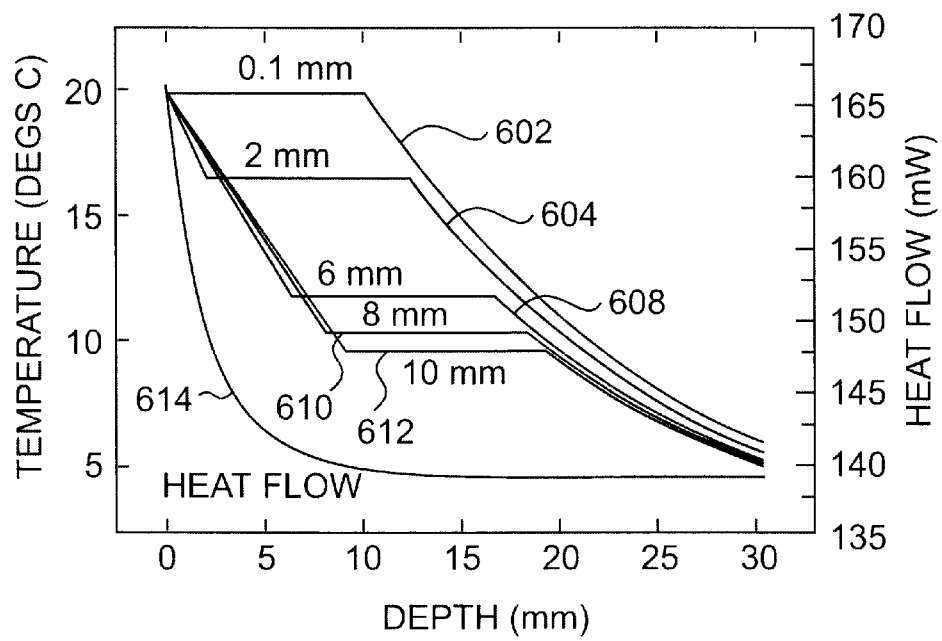
FIG. 6 is a series of calculated plots of the heat flow (lower curve) and the temperature profiles (upper curves) within the sample for five different depths of a buried copper layer.
Figure 7:
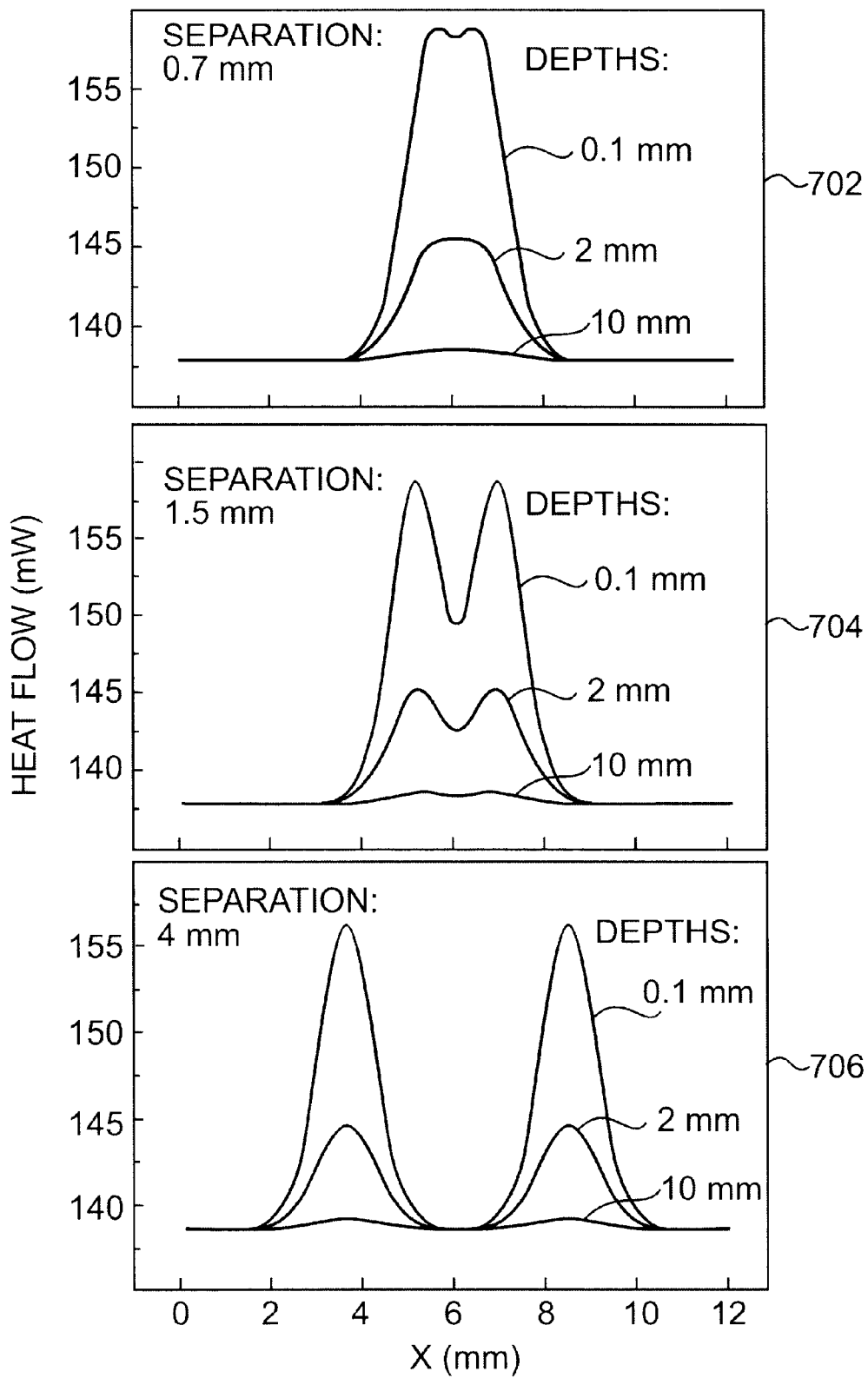
FIG. 7 is a simulated heat flow scan across two particles, buried at three different depths (as labelled).
Figure 8:
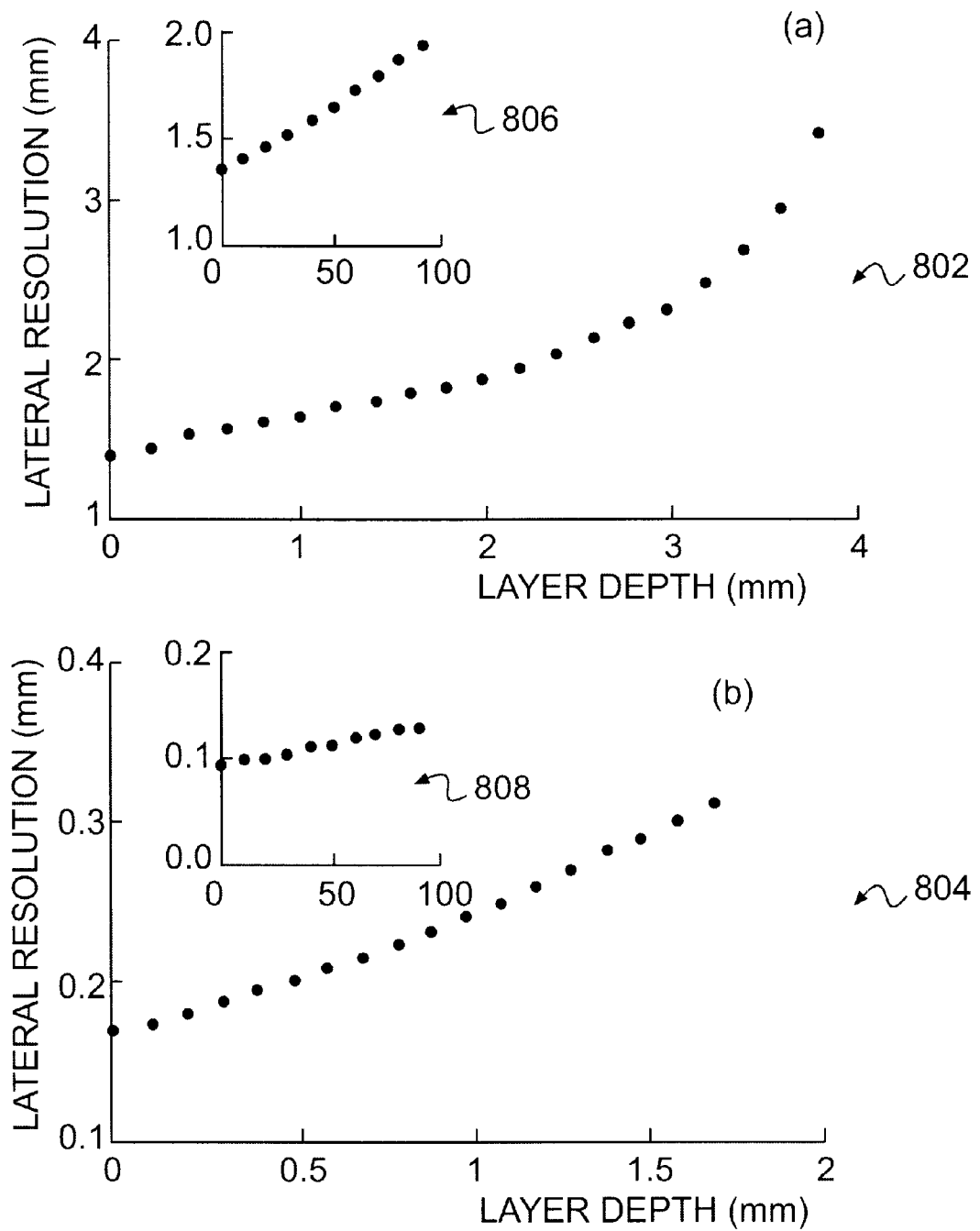
FIG. 8 shows the variation of the calculated lateral resolution as a function of layer depth.

FIGS. 6, 7 and 8 show the results of calculations of temperature profiles directly below the apex of the probe, which is assumed to be just touching the surface. The probe is assumed to have a radius of curvature of 20 μm and a height of 100 μm. The temperature of the probe is assumed to be uniform and constant along the wire length. Heat flows are total heat flows from the probe and obtained by integrating along the shape of the probe. The profiles were calculated for the case of copper inclusions (thermal conductivity=400 W /m.C) embedded in polystyrene matrix (thermal conductivity=0.13 W/m.C). The probe temperature, or $T_0$, was assumed to be 20° C. above ambient.

FIG. 6 shows the temperature profiles 602, 604, 606, 608, 610 and 612 inside the sample for a 10 μm thick copper layer buried at depths varying from 0.1 to 10 μm. Because of the much higher thermal conductivity of the copper, the temperature gradient across the copper layer is much smaller than the temperature gradient in the polystyrene. The temperature gradient refers to the rate of variation of temperature with depth. The lower curve 614 (right hand vertical scale) in FIG. 6 is a plot of the heat flow from the probe for the 10 μm thick copper layer versus the depth of burial of the layer. The heat flow decreases as the layer is buried further away from the surface, and tends to the value of heat flow for a homogeneous polystyrene sample.

FIG. 7 is a series of plots 702, 704 and 706 simulating the heat flow from the probe as the probe is scanned over two copper particles 1 micron in length and 1 micron thick, for increasing separation and increasing depth of burial. As a criterion of lateral resolution, we assume that two particles are resolved if:

$$Q_f(a) \leq Q_{fmin} + (Q_{fmax} - Q_{fmin})\frac{RES}{100}$$

where $Q_{fmin}$ is the minimum heat flow at a given burial depth, $Q_{fmax}$ is the maximum heat flow at a given burial depth, $Q_f(a)$ the heat flow at the trough, and RES is a coefficient of resolution.

If RES is set equal to 20 then the graphs 802 (probe radius $\rho=20\,\mu m$) and 804 (probe radius $\rho=1\,\mu m$) presented in FIG. 8 illustrate lateral resolution as a function of the depth at which the copper layer is buried. The graphs 802 and 804 show that the theoretical lateral resolution is on the order of a micron at the surface, but degrades when the particles are buried further deeply into the bulk. The insets 806 and 808 illustrate alternative curves predicted by an overlapping peaks criterion (20% minimum dip in the heat flow signal between two inclusions, neglecting the effect of noise).

Figure 9:
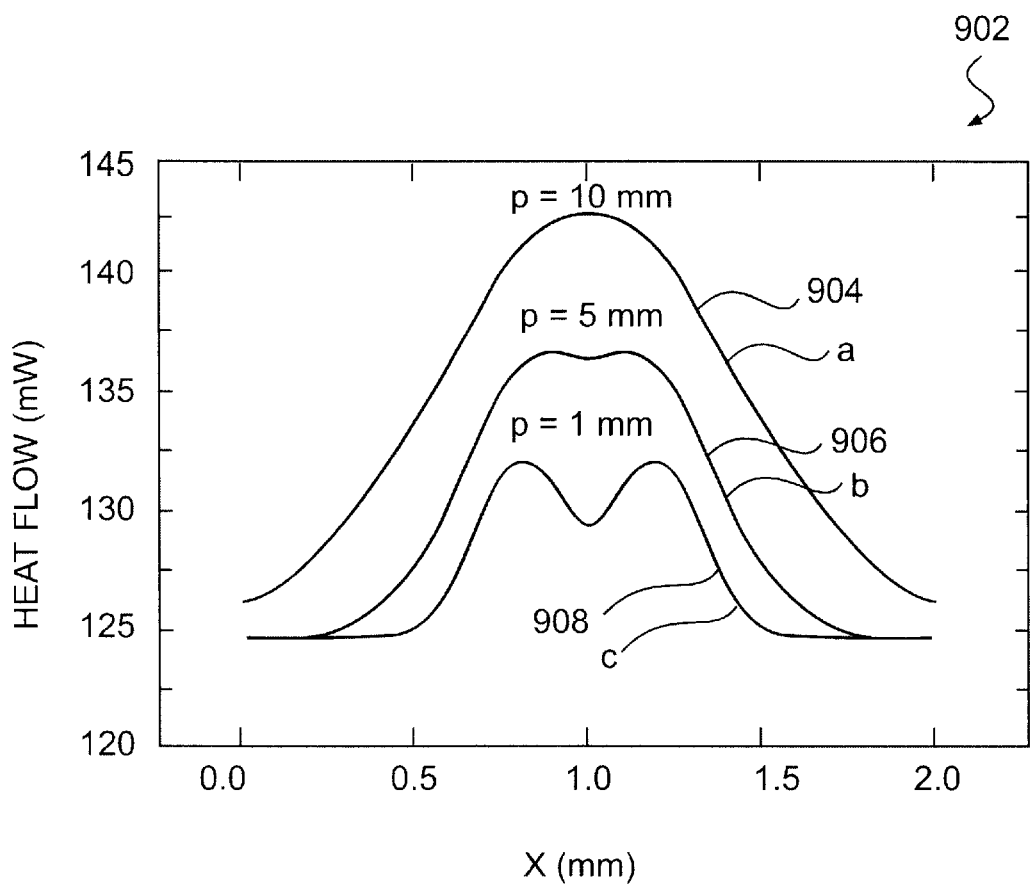
FIG. 9 shows the calculation of simulated heat flows as the probe is scanned across two particles for three different tip radii (as indicated).
Figure 10A:
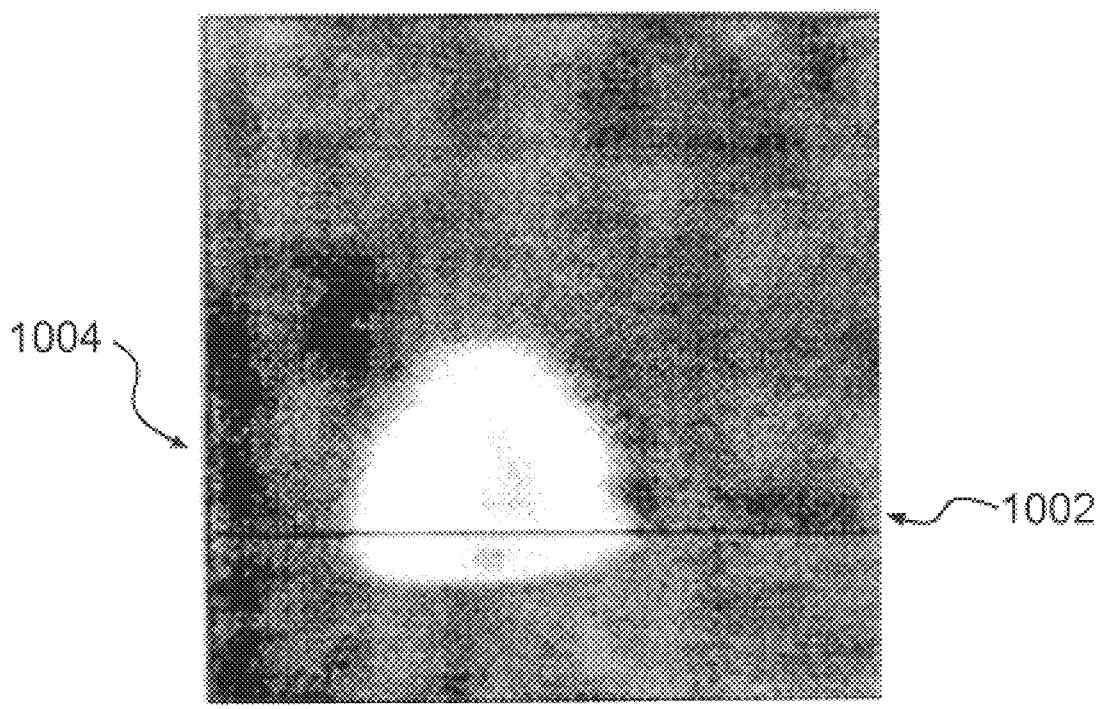
FIG. 10 shows a feedback voltage line scan, for comparison with the calculation shown in FIG. 9.
Figure 10B:
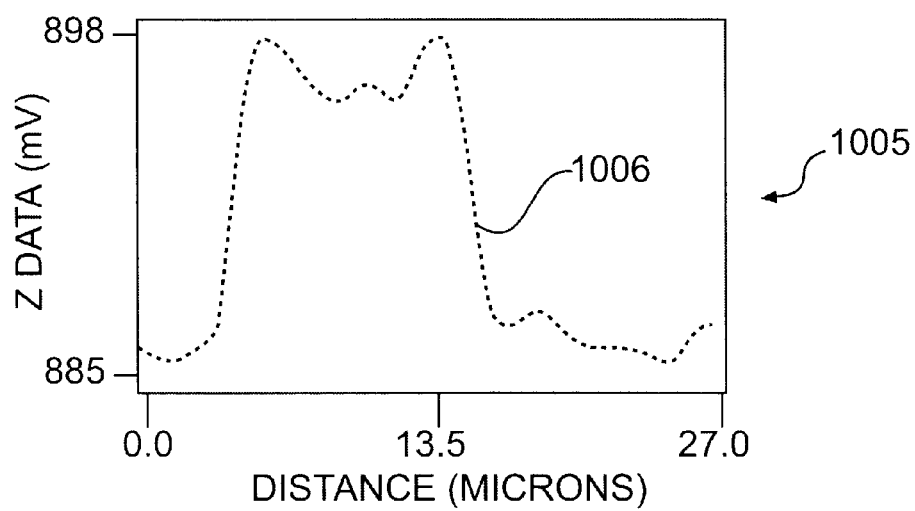

Comparison to Experimental Results:

FIGS. 9 and 10 are a comparison of the simulated heat flows 902, 1002 and 1004 as the probe is scanned across two particles for tip radii of 10 $\mu m$, 5 $\mu m$, and 1 $\mu m$ for curves 904, 906 and 908 (FIG. 9) to experimental data (FIG. 10). The curves 904, 906 and 908 illustrate the improvement of lateral resolution as the radius of the curvature of the probe's tip becomes smaller.

In the scan line 1006 shown in FIG. 10, the bridge feedback voltage excursion ranged from an average of 886 mV to an average of 897 mV. This line scan was obtained for the 1 $\mu m$ thick coating. The feedback voltage when the probe was away from the surface of the sample was 784 mV. The minimum heat flow, into a homogeneous polystyrene region, was calculated to be equal to 165 $\mu W$ and the maximum heat flow (into a region where a copper particle is buried) was 184 $\mu W$. These figures should be compared with theoretical values of 138 $\mu W$ and 158 $\mu W$ obtained for a 10 $\mu m$ thick particle buried at 1 $\mu m$ depth.

Using the two experimental values of heat flow, the calculated value of the thermal conductivity of polystyrene was 0.21 W $m^{-1}$ $C^{-1}$ and the depth of the copper particle was 0.23 $\mu l$. These discrepancies arise from approximations and assumptions in the model and also because the sample geometry is not yet fully controllable. Indeed, the surfaces are not truly flat. Furthermore, from the strength of the thermal signal it is clear that the particles were not all buried at the same depth. It is likely that when the samples were hot pressed, the particles sank at different depths below the surface. The model could be extended to three dimensions, to obtain more reliable thermal data for quantitative interpretation. Using well-known lithography techniques, accurate and reproducible samples could be prepared for further adjustments to the model. Such lithography techniques can be found in M. S. Tyagi, "Introduction to Semiconductor Devices," Section 19.5.2, Wiley (New York 1991), which is hereby incorporated by reference. A full calibration of the instrument would then be possible and quantitative interpretation of the recorded data in terms of thermal conductivity measurements, for example, could then be achieved.

EXAMPLES

The following examples illustrate applications of the thermal probe to obtain a map of surface calorimetric data, with a lateral resolution on the order of a micron, and a probed volume of material on the order of a few $\mu m^3$. They include:

mapping at the sample surface variations in thermal conductivity and in thermal diffusivity, when the temperature-modulation mode is used;

sub-surface imaging—in principle, by varying the frequency of the evanescent temperature wave used, the depth to which the evanescent waves penetrate (and hence the thickness of the region being imaged) can be controlled: and localized calorimetric analysis of micron-sized regions, as a step towards mapping thermally activated near-surface processes such as glass transitions, meltings, cure reactions, recrystallizations, and degradations.

The use of the present invention in the characterization of polymer blends is of particular importance, because of the wide use of polymer blends in adhesives and coatings. In such applications, changes in surface properties as a function of temperature are of critical importance.

For example, film-forming emulsion polymers are widely used in paper coatings, latex paints, water-based adhesives and other applications. The properties of the film itself depend upon the way in which the individual latex particles are able to integrate. The mechanisms of film integration from latex particles, and the interface development between two compatible polymers are currently the subjects of significant study by polymer scientists. For example, the properties of the particle-particle interface affect the performance of the resulting coating, in the case of films used in paper coating, latex paints and water-based adhesives.

The following examples are provided to illustrate certain embodiments of the present invention. They are not to be construed as limiting the invention in any way.

Example 1

This example illustrates the use of the present invention to map heterogeneous samples with heterogeneous thermal properties. FIGS. 11A, 11B, 11C and 11D were obtained with the scanning probe microscope of the present invention operated in the constant temperature mode and the probe temperature set at 40° C. The thermal contrast images were computer-generated, using the feedback voltage $V_b$ applied to the Wheatstone bridge circuit 204. Because of the relatively slow scan speed (usually 100 $\mu m\ s^{-1}$), steady state (thermal equilibrium between the probe and the region of the sample whose temperature is affected by the probe) was reached at each point, so that the image contrast was indeed determined by the value of the heat flow. At each sampling point a certain volume of material was heated. This volume can be approximately delimited by the thermal contact area and an effective depth determined by the temperature gradient below that contact area. The heat flow from the probe into the sample characterizes the thermal conductivities of the material within the heated volume.

Samples were prepared in a well-known manner by spraying polystyrene substrates with fine copper particles (nominally less than 1 micron diameter). The samples were then hot-pressed between glass slides at a temperature just below the melting temperature of polystyrene, and then were coated with a formvar film cast from a solution in chloroform, or coated with layers of polystyrene films 17 $\mu m$ thick (in this case they are hot-pressed a second time).

Figure 11A:
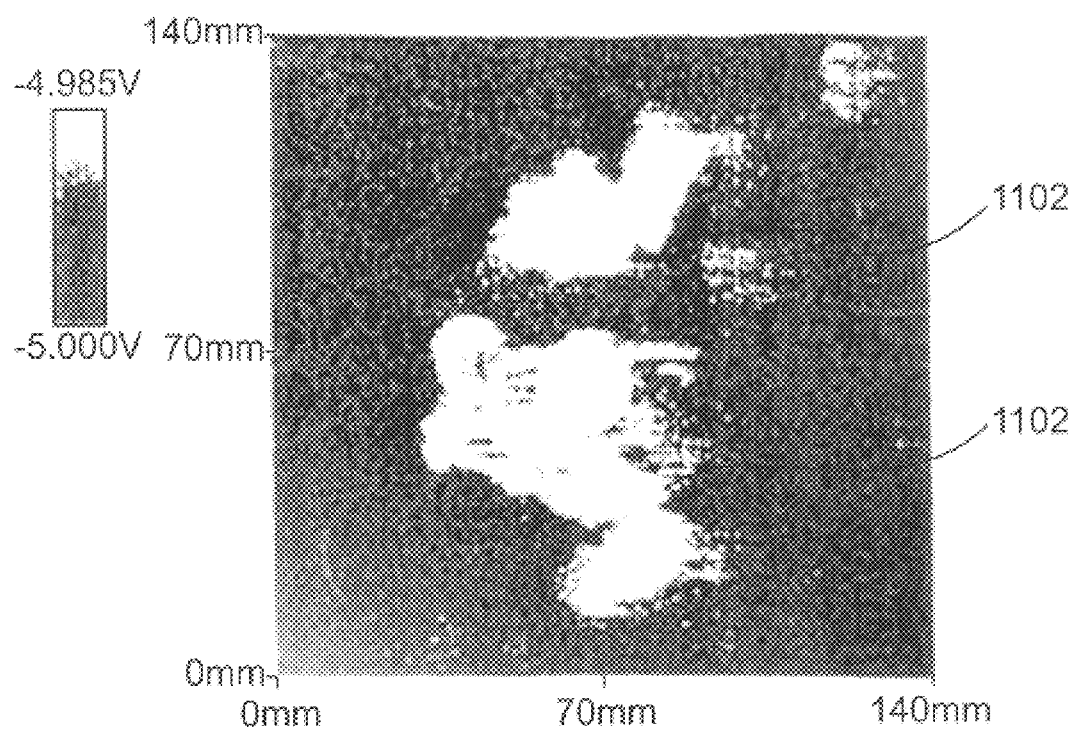
FIGS. 11A–11D are subsurface thermal images of buried particles.
Figure 11B:
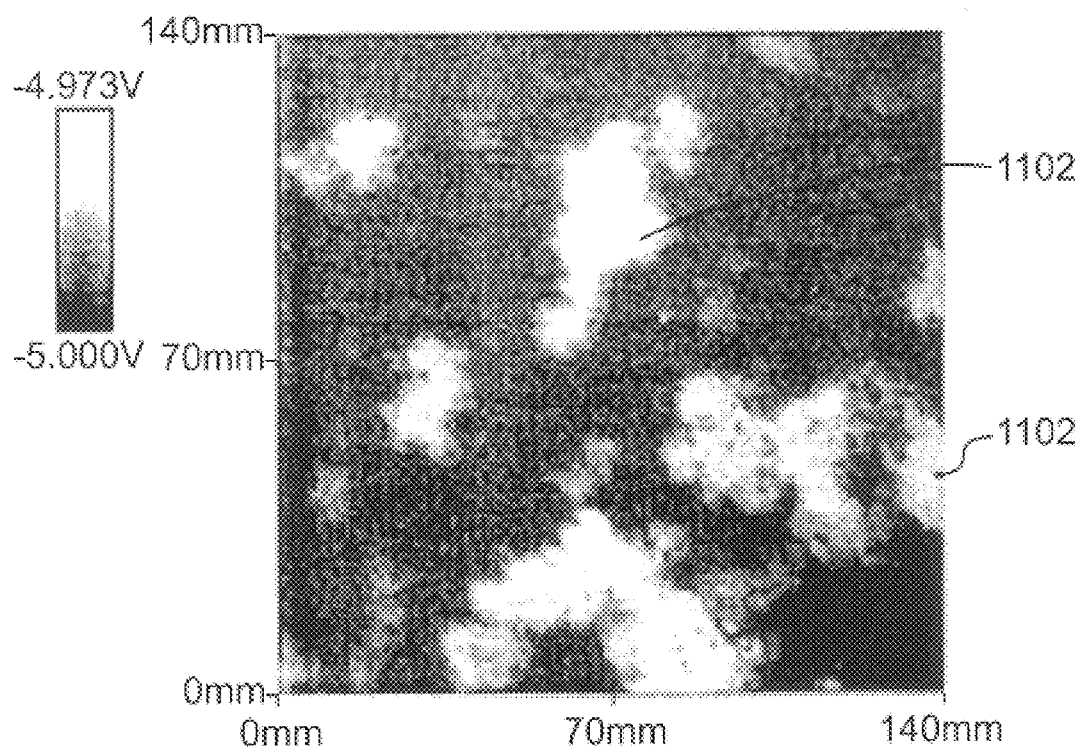
Figure 11C:
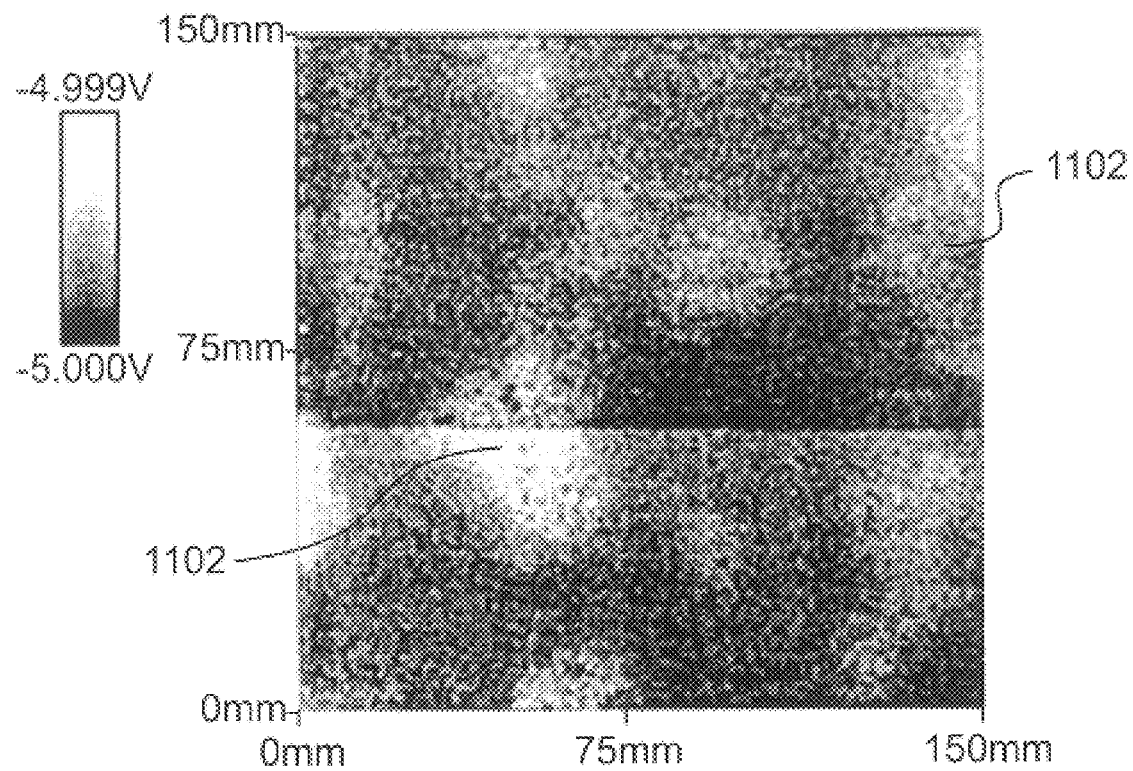
Figure 11D:
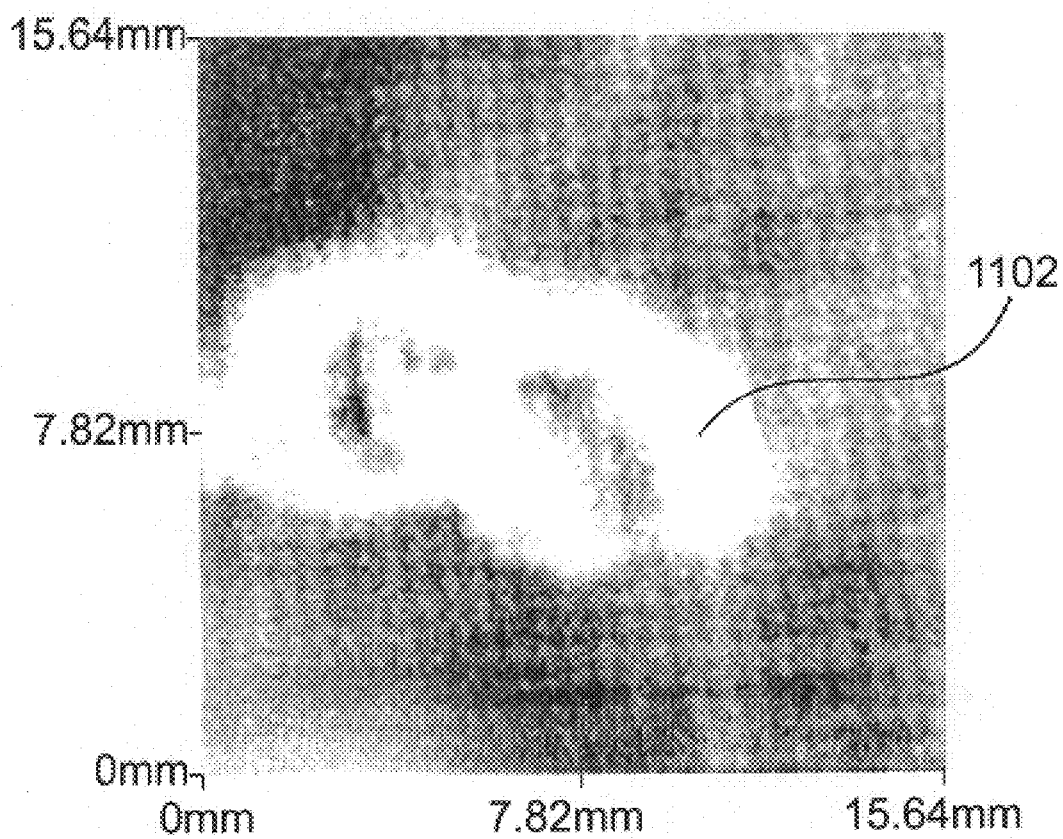

FIGS. 11A, 11B and 11C are thermal images obtained when scanning samples with a coating thicknesses of 400 nm, 1 $\mu m$ and 4 $\mu m$, respectively. They show areas of high thermal conductivity 1102, randomly shaped, and of sizes varying from a few microns to a few tens of microns. These figures show aggregates of the original particles, which have not fully dispersed below the surface of the samples. The particles are clearly detected and show brighter in the thermal contrast, indicating that they draw more heat from the probe, through the formvar film, because of the higher thermal conductivity of the copper. Thus at each point, the sampling volume heated extends deeply enough to include the buried particles. However, as indicated by the scale bars, the feedback voltage excursion diminishes as the thickness increases. Deeply buried particles do not show, as illustrated by FIG. 11D. Here a particle can be faintly seen within this sample, which had been covered with a 17 $\mu$m polyester film. We conclude that with a probe temperature of 40° C., the "depth of vision" of the probe is a few microns. This is limited by the background noise (including ambient thermal fluctuations and electronic noise).

Example 2

This example demonstrates the use of the present invention for the study of immiscible polymer blends systems, including a Poly(vynil chloride) [PVC]/Polybutadiene [PB] blend, a Poly(ethylene oxide) [PEO]/Polybutadiene [PB] blend and a Poly(methyl methacrylate) [PMMA]/Chlorinated polyethylene [CPE] blend. The blends were cast from solutions on microscope glass covers with a 50/50 percentage weight. After drying, films about a hundred microns thick are formed.

In each system, the two polymers involved segregate, being immiscible: one forms a matrix and the other forms island-like domains. The two phases in each sample were identified by mapping the thermal conductivity variation across the surface of the sample using the thermal probe, operated in the closed loop mode at a constant temperature of 40° C. The signal was obtained from the feedback voltage applied to the controlling bridge in order to maintain a constant probe temperature. The contrast at each point represents variations in thermal conductivity across the sample.

Figure 12:
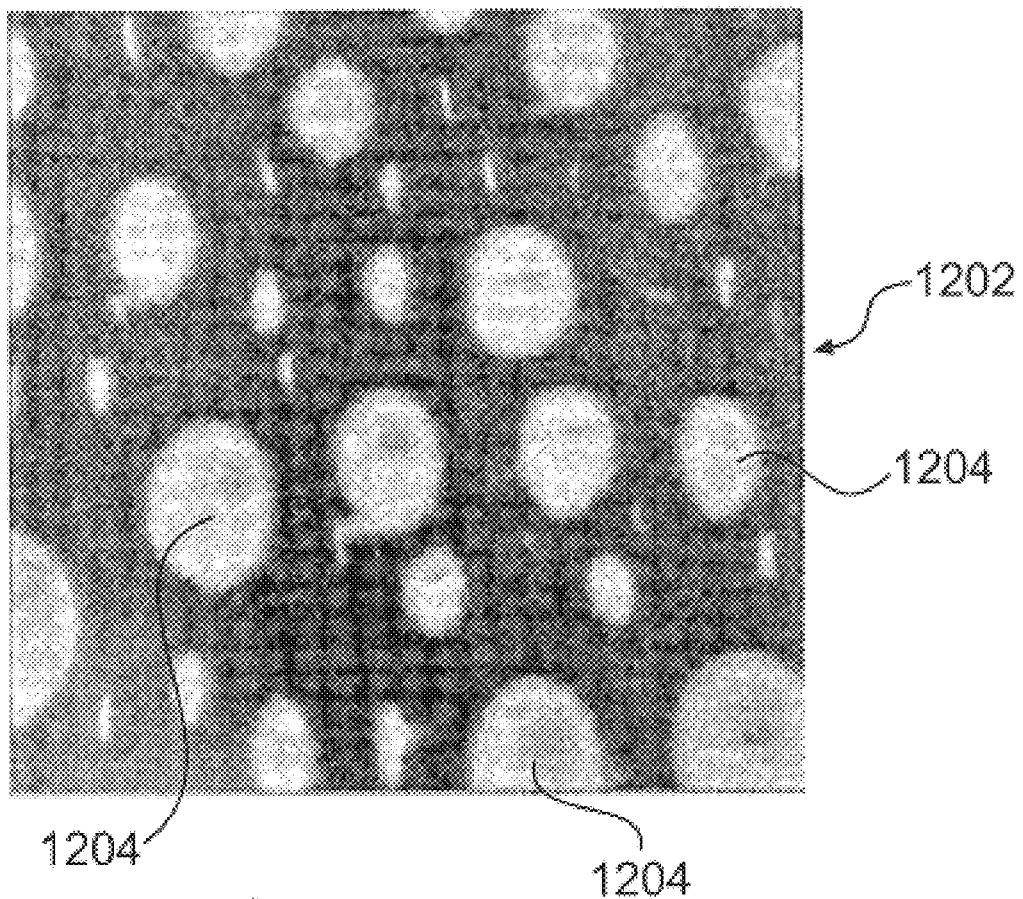
FIG. 12 is a thermal image of a PVC/PB immiscible blend.

FIG. 12 is a thermal image 1202 of a PVC/PB blend obtained at a zero modulation frequency. The image contrast is a representation of thermal conductivity variations across the sample within a depth of a few microns. The two phases are clearly apparent: PB, having a higher thermal conductivity (0.24 J/sec.m.K) than PVC (0.14 J/sec.m.K), is identified by the brighter island-like domains 1204 of higher thermal conductivity. Thus in this particular system, PB segregates into domains 1204 of diameter up to about 50 $\mu$m in a matrix of PVC.

Figure 13A:
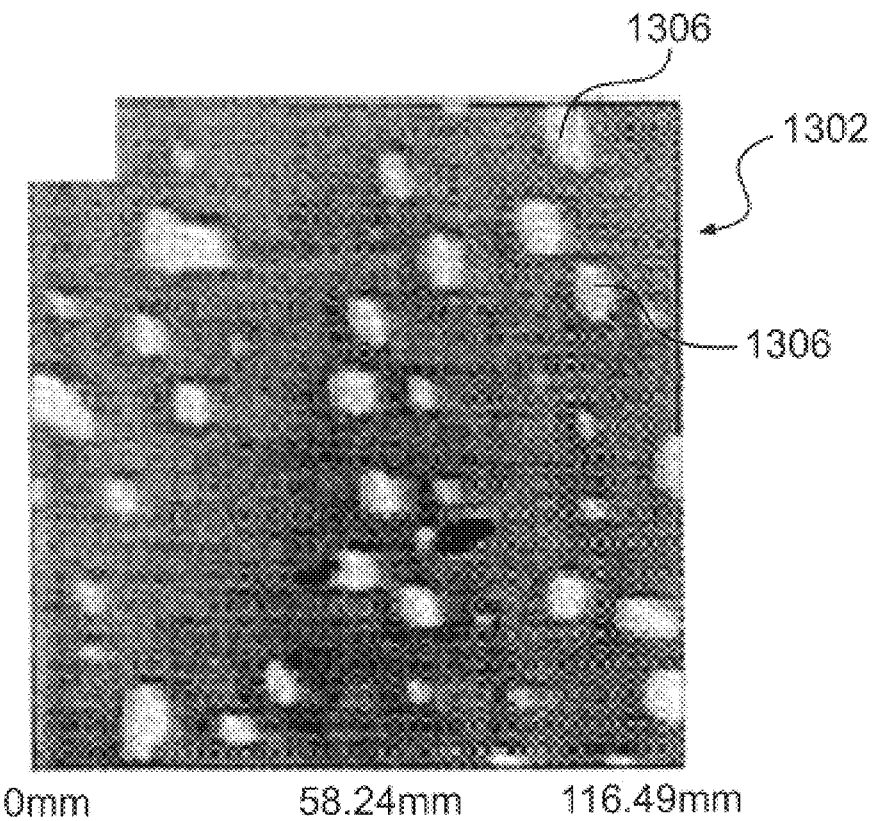
FIGS. 13A and 13B are thermal images of a PMMA/CPE blend.
Figure 13B:
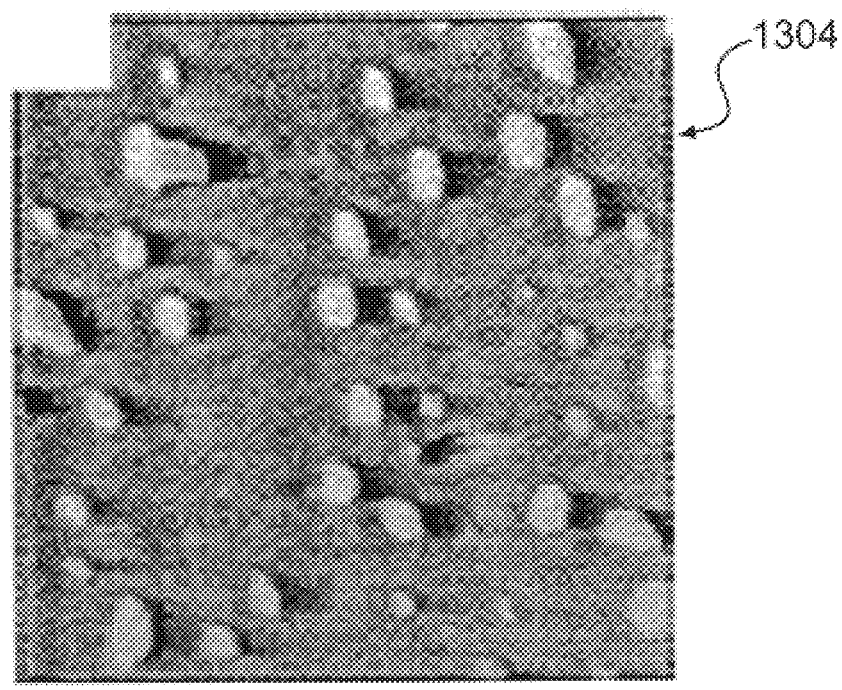

FIGS. 13A and 13B are images 1302 and 1304 of a PMMA/CPE system using unmodulated and modulated thermal probes. For FIG. 13A, the probe was operated in the closed loop mode at a temperature of 40° C. For FIG. 13B, a 10 kHz fluctuating temperature of about 5° C. was superimposed on the 40° C. operating temperature. In FIG. 13A, the contrast corresponds to variations in thermal conductivity. Thus in this particular system, PMMA, which has a higher thermal conductivity than CPE (0.193 against 0.144 $J.S^{-1}.m^{-1}.K^{-1}$), segregates again into island-like domains 1306 in a matrix of CPE. In FIG. 13B, contrast arises from the phase shift of the AC voltage across the probe as it is scanned. The contrast in FIG. 13B represents variations of thermal properties, which include diffusivity, across the sample within a depth (below the surface) equal to the thermal diffusion length, as determined by the modulation frequency.

Example 3

Figure 14A:
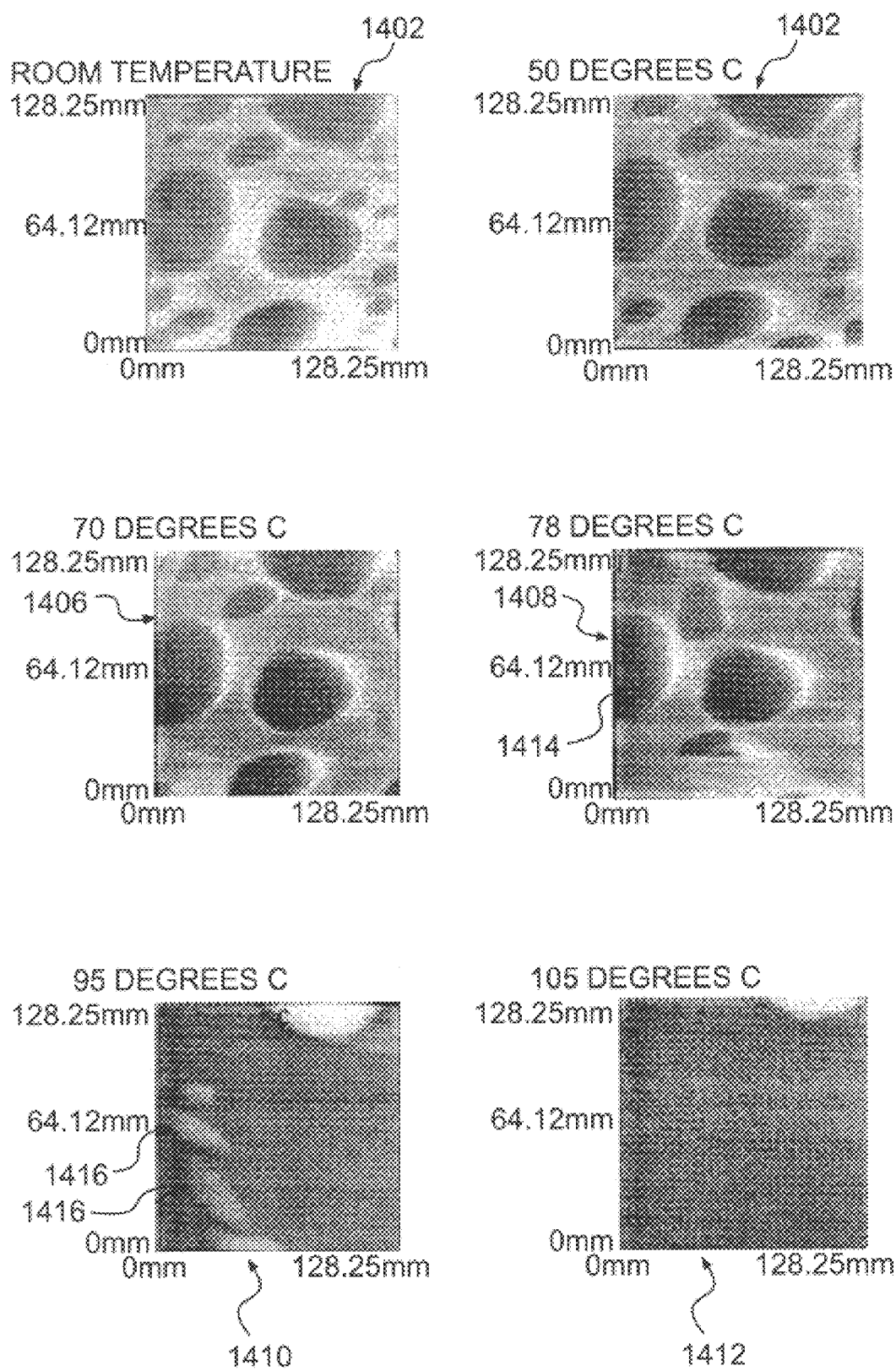
FIGS. 14A and 14B illustrate temperature- and probe-induced effects on domains in a PVC/PB blend.
Figure 14B:
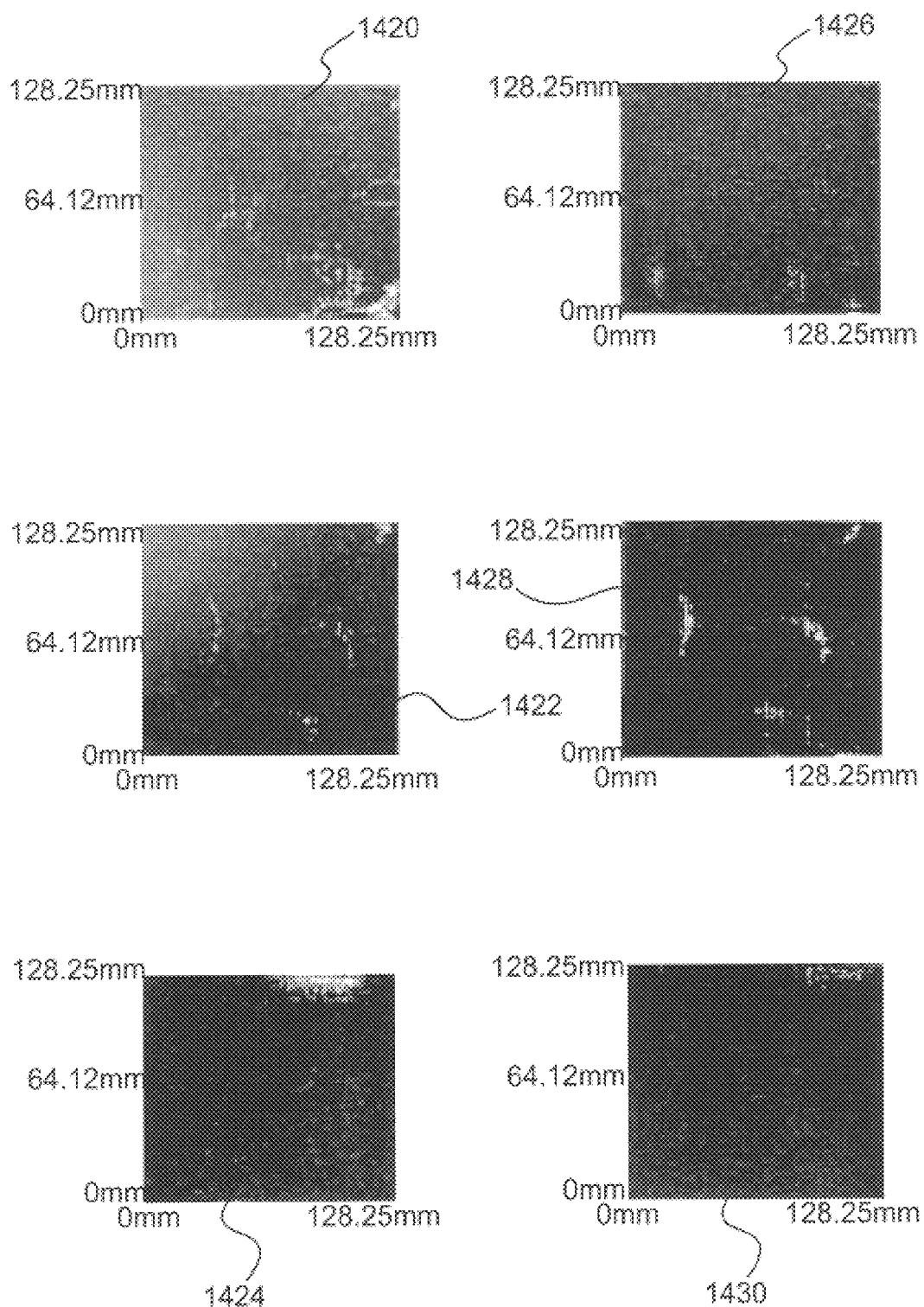

This example illustrates the use of the present invention to follow, in real time, the behavior of PVC domains in a PVC/PB blend as a function of temperature, using a temperature-controlled hot stage. The same area was scanned at increasing hot stage temperature, which was maintained constant during each scan. The probe was operated in the closed loop mode, at a constant temperature of 85° C. Images obtained at room temperature (RT), 50° C., 70° C., 78° C., 95° C. and 100° C. are shown in FIG. 14A (1402, 1404, 1406, 1408, 1410 and 1412). (The temperature of the sample is shown in the upper right-hand corner of each image.) FIG. 14B also shows images (1420, 1422, 1424, 1426, 1428 and 1430) of PVC domains in a PB matrix as a function of increasing temperature. As the temperature is increased up to about 70° C., little change to the system is observed, although small domains can be seen to move and are absorbed into neighboring larger ones. As the temperature is further increased large domains move outside the field of view. One domain 1414 is clearly seen to have broken up into smaller ones 1416. The reversal in contrast in the higher temperature images is due to the temperature of the stage becoming higher than the average temperature along the probe (set at 85° C.).

At and above room temperature, PB is in the rubbery state (the glass transition takes place at −65° C.) and up to about 70° C., PVC is in the glassy state. The probe induces a local phase transition in PVC and further softening of the PB This facilitates the movement of small domains. Above 70° C., PVC becomes rubbery and this probably accounts for the break up of the PVC domain under the action of the scanning probe. Above about 90° C., PB is in an almost liquid state, and the large PVC domains are easily moved by the probe to beyond the field of view.

Example 4

This example shows the use of the present invention to perform spatially localized thermal analysis. Instead of using a heating stage, precisely-defined regions of the sample were heated through the temperature range of interest. The heat was supplied by the probe itself. The probe was placed at a fixed location on the surface of a sample (see FIG. 3B), and both sample probe and reference probe were subjected to a temperature ramp with an added temperature oscillation of about one degree amplitude.

A number of polymeric materials were investigated. The transitions were more sharply identified in the phase signal. Some of the results obtained are presented here in the form of plots of the phase, or the first derivative of the phase, against temperature. Data from bulk samples of the same materials obtained from conventional bulk thermal analysis techniques (DSC and thermogravimetric analysis (TGA)) are also presented for comparison in Table I.

Figure 15:
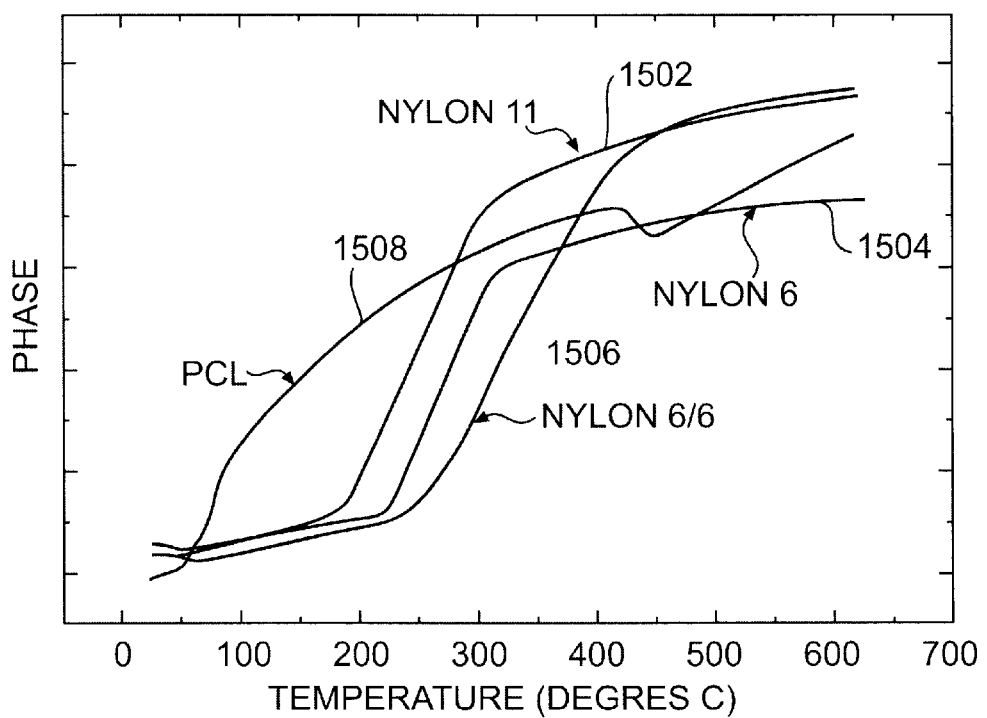
FIG. 15 shows the phase signal recorded for three types of nylons, and for PCL.

FIG. 15 shows the phase signal recorded for three types of nylons (11 (1502), 6 (1504), and 6/6 (1506)) and polycaprolactone (PCL) 1508. Melting points are identified by a sharp change in the slope of the signal. Table I shows that these changes correspond to the melting points of the materials. The changes observed at higher temperatures are probably associated with decomposition. For example, there is a good correlation with the thermal decomposition temperature range obtained from TGA shown in Table I.

Figure 16:
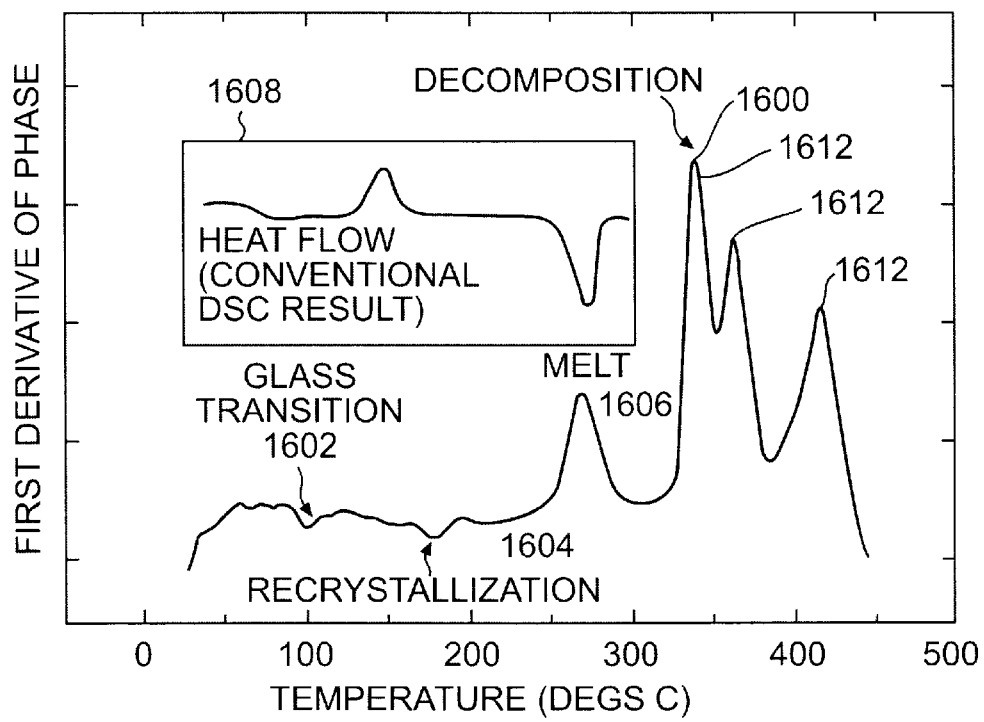
FIG. 16 is a plot of the derivative of the phase signal of PET. The inset shows a typical heat flow signal obtained using conventional bulk differential scanning calorimeter.

FIG. 16 is a plot of the first derivative of the phase versus temperature obtained for quenched poly(ethylene terephtalate) (PET), covering a region of temperature over which degradation occurs. Below 300° C. three events are clearly identified. These are interpreted as the glass transition 1602, recrystallization 1604 and melting 1606, respectively, as shown in FIG. 16. The inset 1608 in FIG. 16 is a typical plot of bulk heat flow versus temperature obtained using conventional DSC on a bulk sample from the same material. The inset shows that the same events are recorded using conventional bulk DSC. However, while the melting transition occurs over the same range of temperature in the signal obtained using a localized scan as in the bulk signal, the glass transition and recrystallization occur at higher temperatures in the localized signal as compared with the bulk signal. This may be due to surface effects, and to the small volume of material involved.

At temperatures above about 350° C., decomposition 1610 is observed. This is consistent with bulk TGA data. Furthermore the three peaks 1612 observed during degradation may be associated with the breaking of specific chemical bonds. Degradation refers to a stage along the process which can eventually result in complete decomposition.

Example 5

Figure 17A:
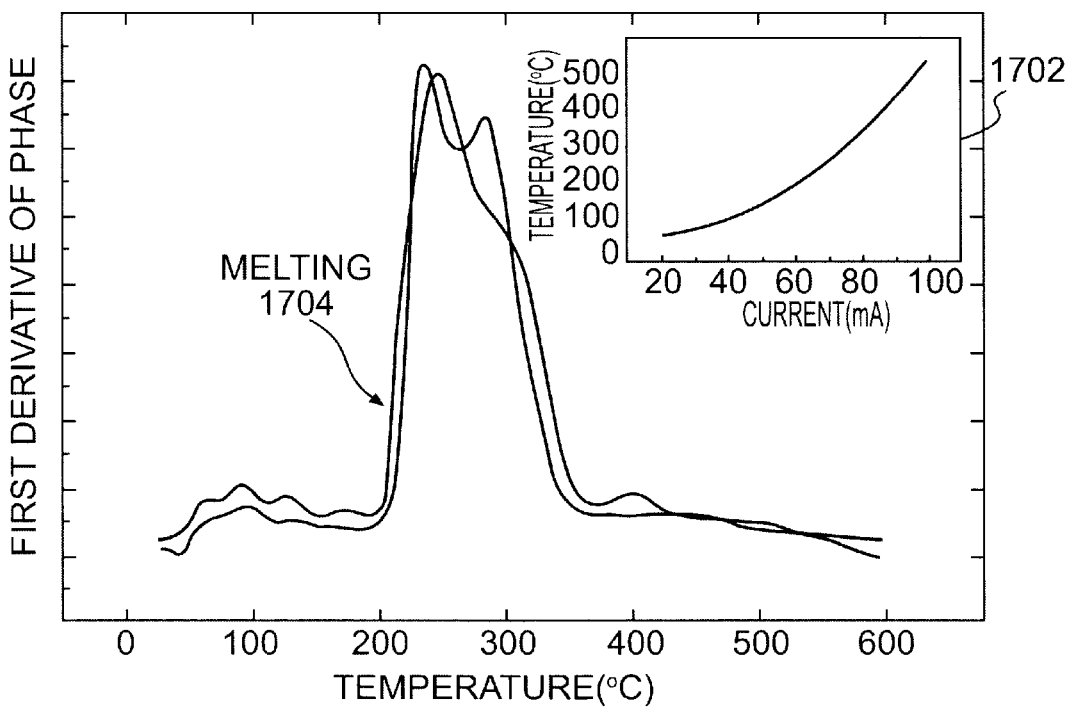
FIGS. 17A–17E are plots of the first derivative of the phase, which illustrate localized melting transitions for a number of polymers. The melting temperature range as observed with conventional calorimetry is given in brackets as follows.
Figure 17B:
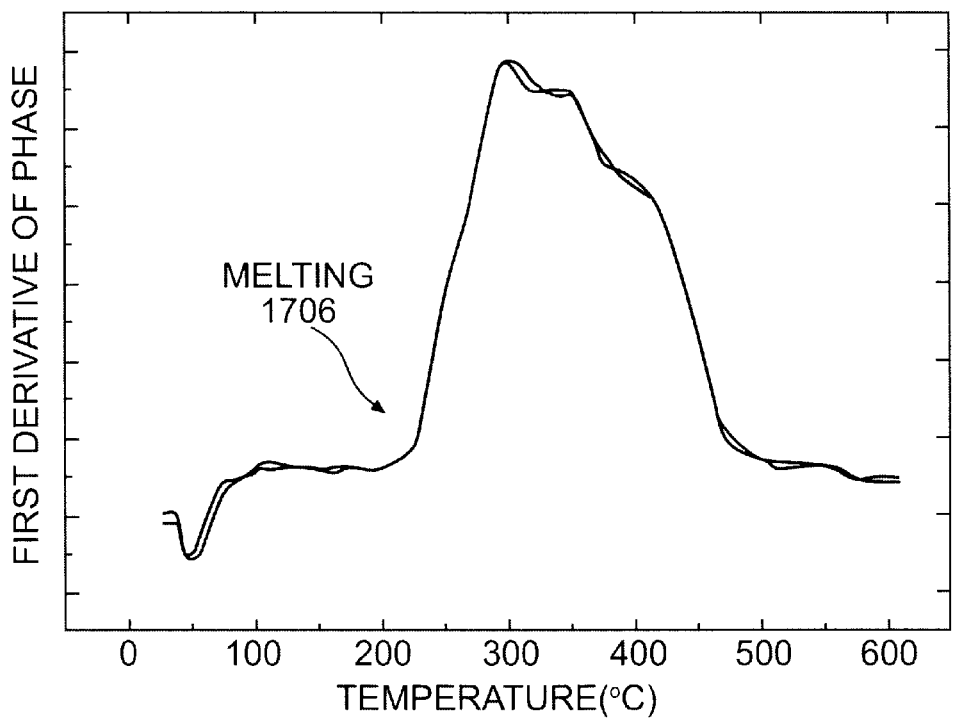
Figure 17C:
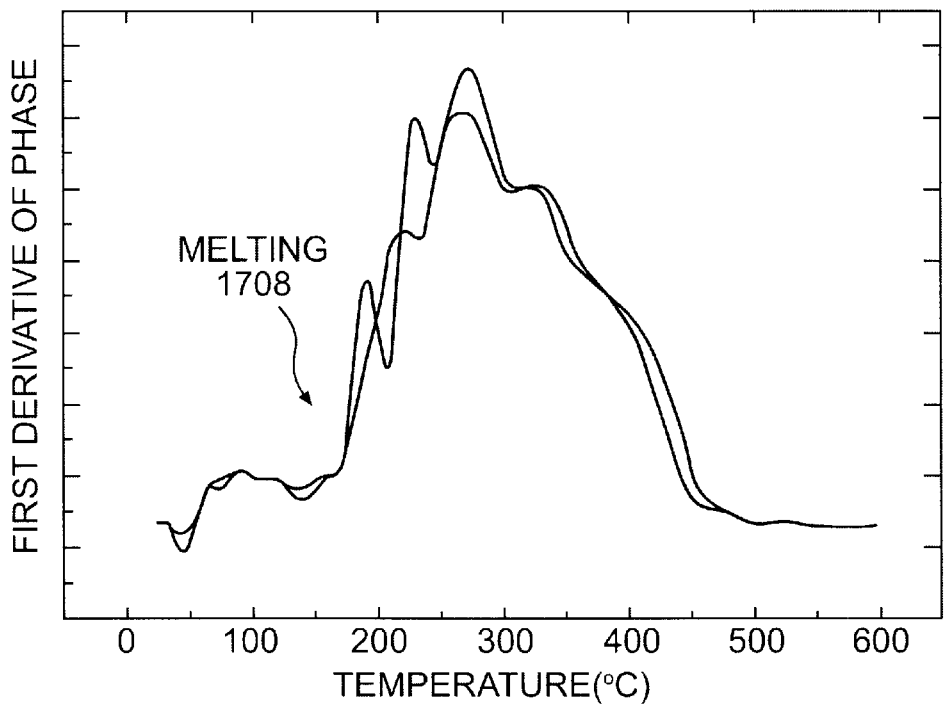
Figure 17D:
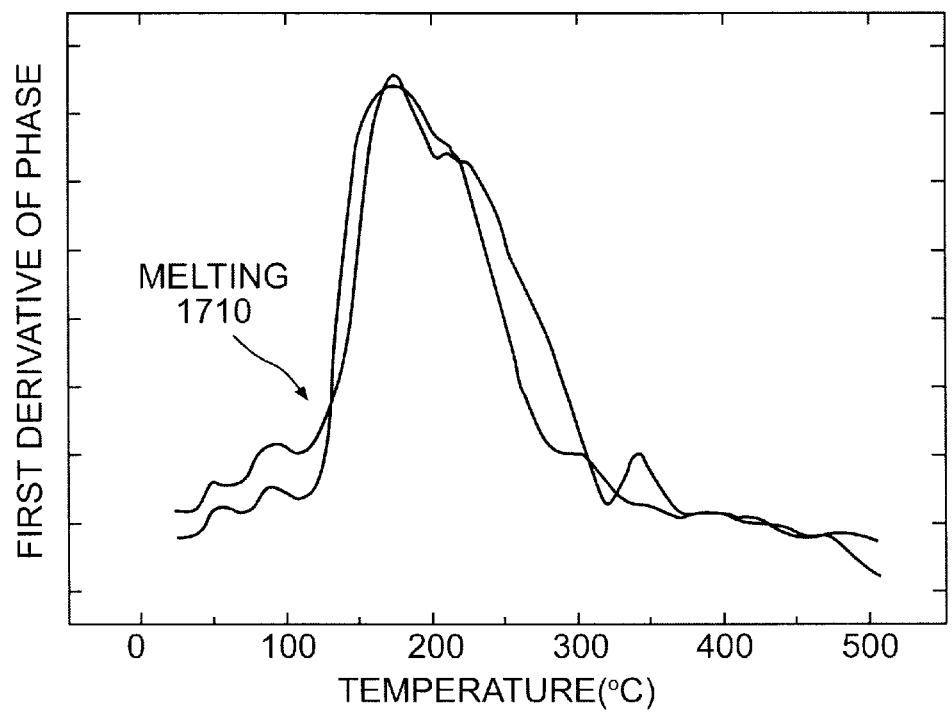

This example shows that the phase signal can be used to identify transitions. Some of the results obtained are presented here in the form of plots of the first derivative of the phase vs. temperature. For each material, two or three plots were obtained at two different locations on the sample (the locations were separated by about 1 mm). These plots demonstrate the reproduceability of the results. These data can be compared to the data from bulk samples of the same materials obtained from conventional bulk thermal analysis techniques, shown in Table I. The data described in this example were obtained by linearly increasing the current in the probe, not the temperature of the sample. Thus the rate of change of temperature is not constant. An example of a temperature/current characteristic used for data linearization is shown in the inset 1702 to FIG. 17A. Although a much faster temperature ramp can be used for the localized analysis of this example than is possible for bulk modulated differential scanning calorimetry, the average value of the heating ramp was only 15° C./min, for a more reliable comparison with bulk data.

Figure 17E:
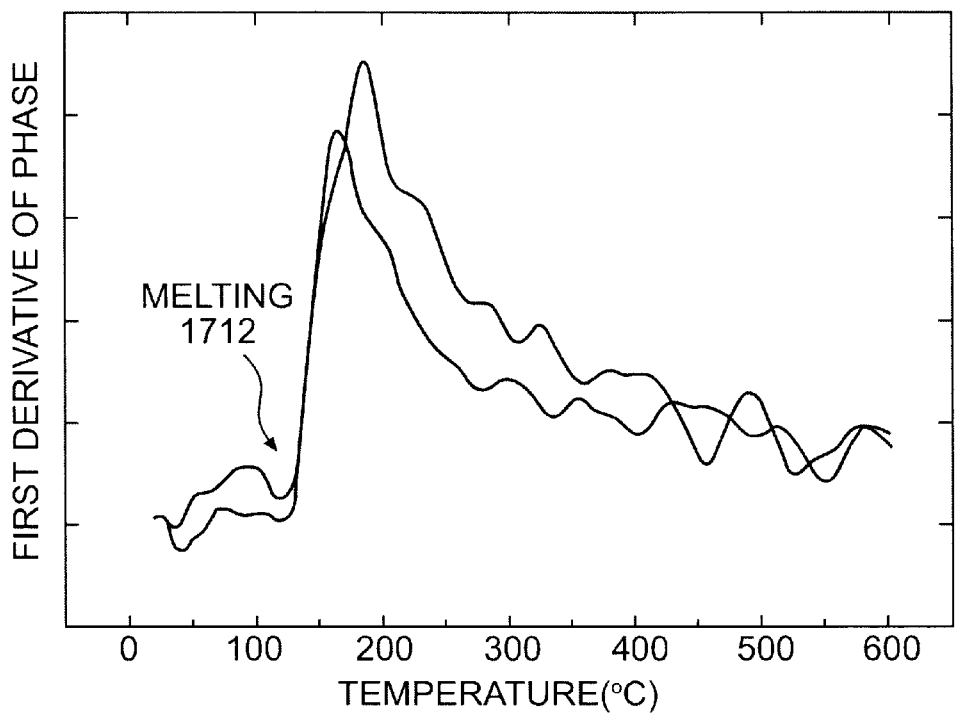

FIGS. 17A–17E are a series of plots illustrating localized melting transitions for nylon 6 (FIG. 17A, feature 1704), for nylon 6/6 (FIG. 17B, feature 1706), for nylon 6/10 (FIG. 17C, feature 1708), for high density polyethylene (FIG. 17D, feature 1710) and for polyvinylidene fluoride (FIG. 17E, feature 1712). Melting transitions 1704, 1706, 1708, 1710 and 1712 are identified by a sharp change in the slope of the phase signal as the temperature is increased. These changes correspond to the known melting points of the materials as obtained by conventional calorimetry and shown in Table 1.

Figure 18A:
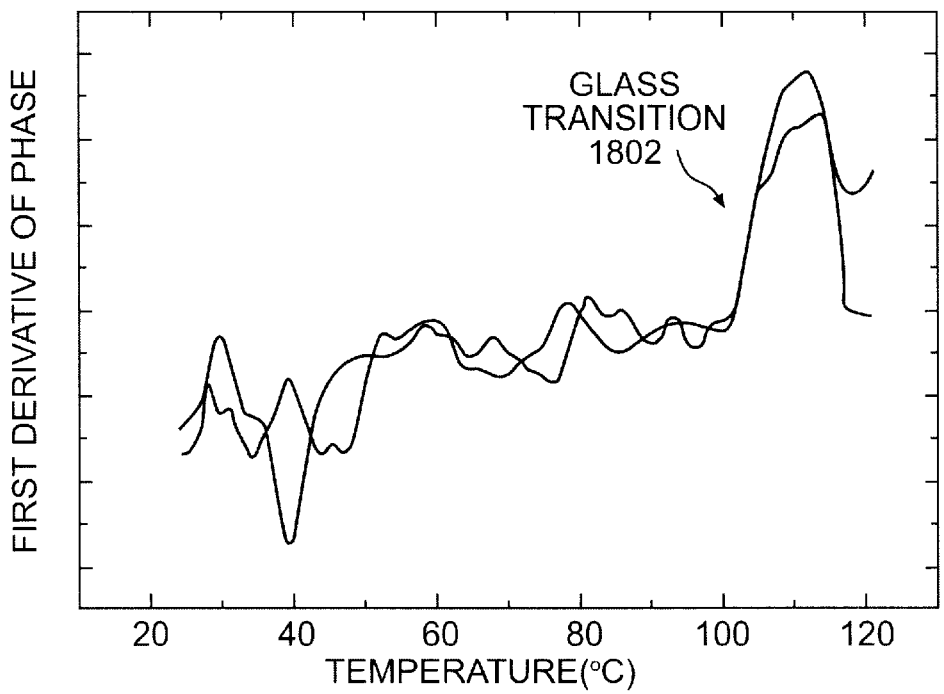
FIGS. 18A–18B are plots of the first derivative of the phase versus temperature, illustrating a localized glass transition for two polymers.
Figure 18B:
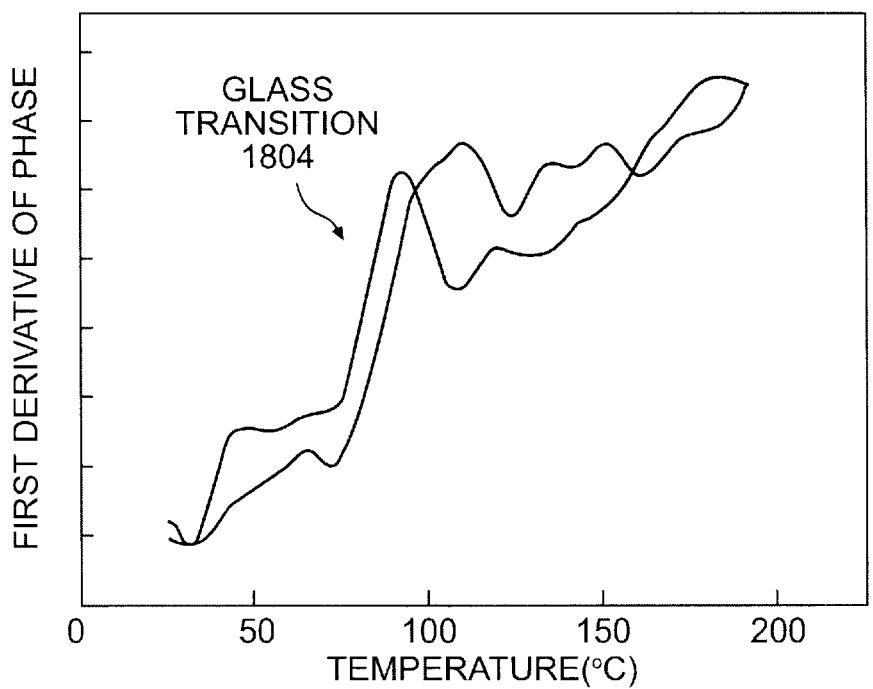

FIGS. 18A–18B are plots illustrating localized glass transitions for polystyrene (FIG. 18A, feature 1802) and for poly(ethyl methacrylate) (FIG. 18B, feature 1804). The transition to a rubbery state is identified by a change in the slope of the phase signal, which occurs at a temperature similar to the transition temperature obtained by conventional calorimetry. However, this transition is not as pronounced as melting transitions.

Figure 19:
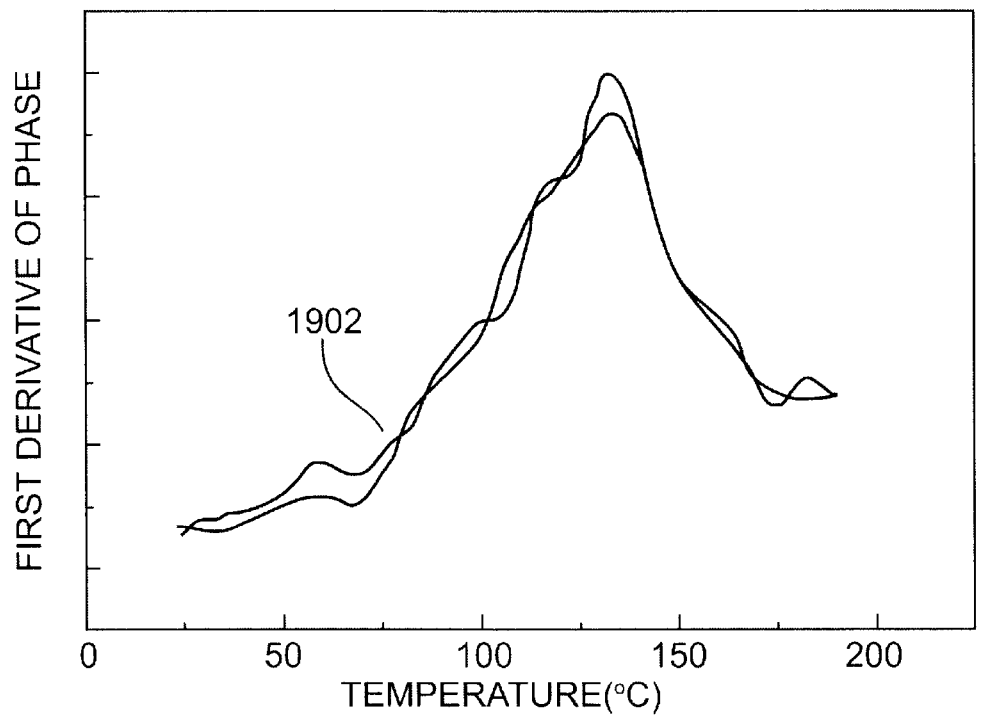
FIG. 19 shows plots of the first derivative of the phase versus temperature obtained for the PEO-PS-PEO block copolymer system.

FIG. 19 shows plots obtained for the block copolymer system PEO-PS-PEO, where PEO is poly(ethylene oxide) (melting temperature in the range 60 to 70° C.) and PS is polystyrene (glass transition in the range of 90 to 110° C.). One transition 1902 only is observed, with no detectable separation of transition events associated with individual polymers. This indicates that individual polymers are not present as separate chemical identities.

Figure 20A:
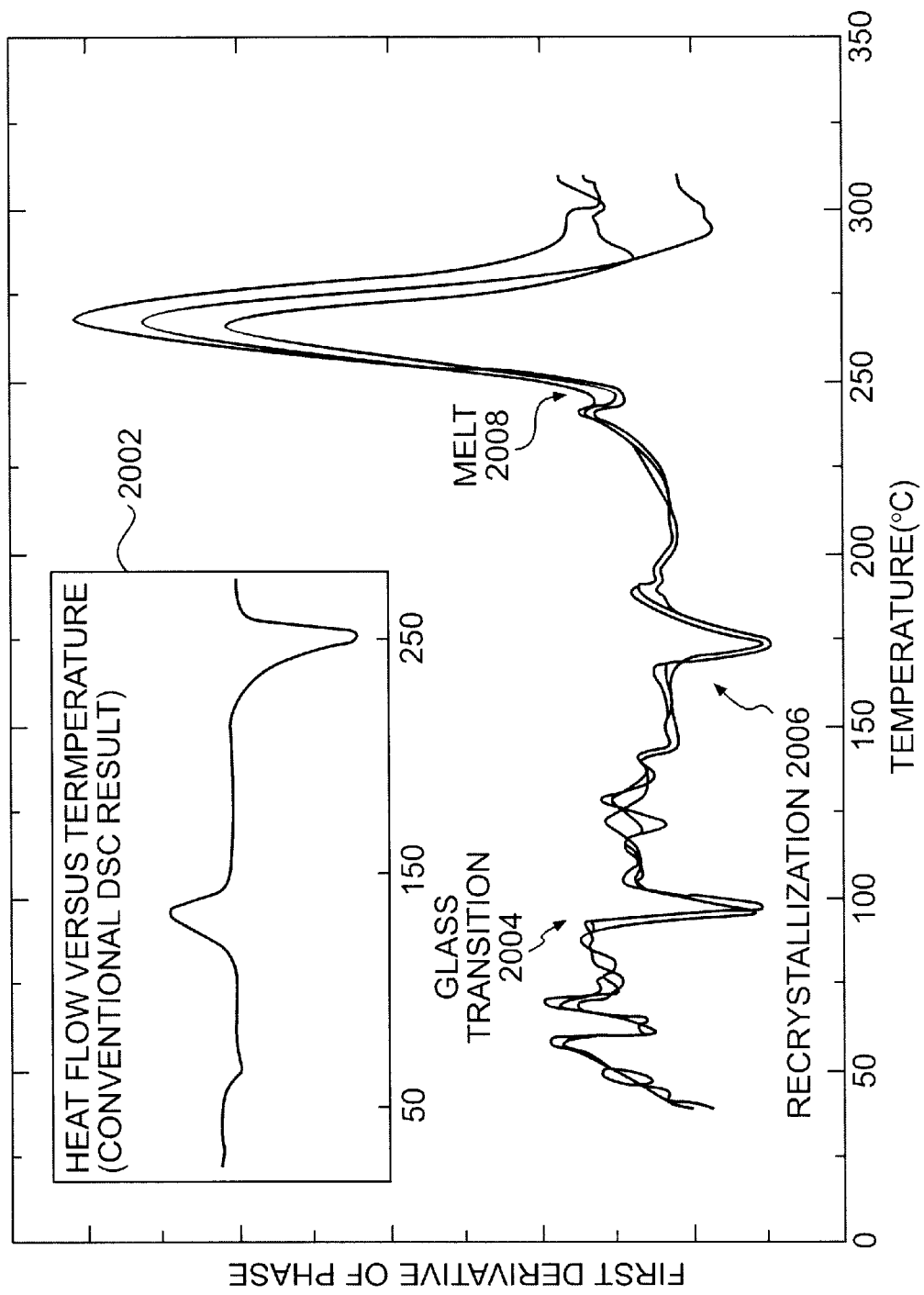
FIG. 20A shows plots of the first derivative of the phase signal versus temperature obtained at three different locations on a quenched poly(ethylene terephtalate) sample.
Figure 20B:
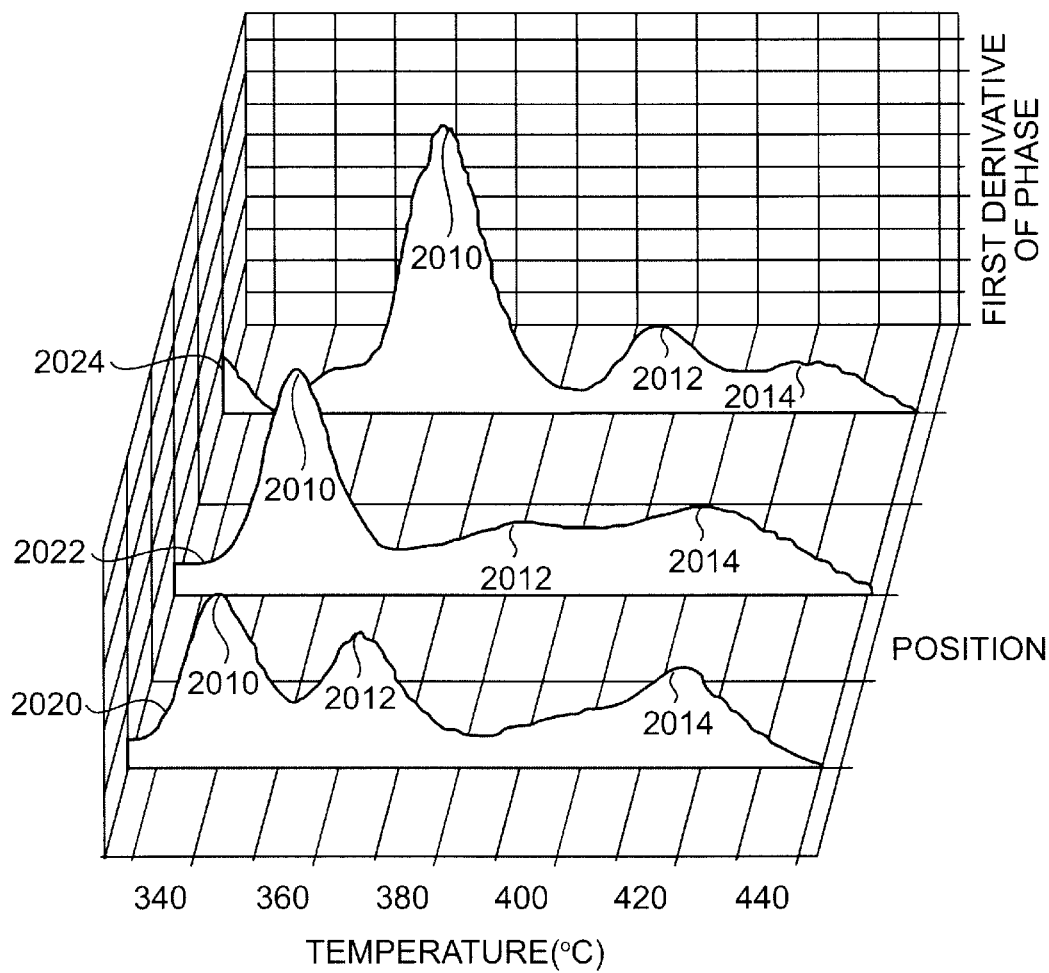
FIG. 20B are plots obtained in a temperature range in which the sample degrades, showing three reproducible peaks.

FIG. 20A shows plots recorded at three different locations on the same sample of quenched poly(ethylene terephtalate) (PET). Three reproducible events are clearly identified in each plot. These are interpreted as the glass transition 2004, recrystallization 2006 and the melting transition 2008. The inset 2002 in FIG. 20A is a typical plot of bulk heat flow versus temperature obtained using conventional DSC on a sample from the same material, illustrating the same transitions in bulk PET. FIG. 20B shows plots 2020, 2022 and 2024 obtained for temperatures above 300° C., covering the temperature range at which degradation occurs. Three peaks (features 2010, 2012 and 2014) are observed which are tentatively assigned to the breaking of particular bonds.

The event associated with the glass transition in PET does not show in the phase signal the same way as it does in the case of polystyrene (FIG. 18A, feature 1802) or in the case of poly(ethyl methacrylate) (FIG. 18B, feature 1804). This may be because when a polymer goes through a local phase change, such as a glass transition or a melting transition, it softens. This leads to changes in the area of mechanical contact of the probe, so that the recorded signal is affected. This effect must be assessed and deconvoluted from effects due to changes in thermal conductivity/diffusivity, or to heat exchanges (endotherms and exotherms) associated with phase changes.

Further Comments

Although all the characteristic plots presented in these examples were obtained by ramping the temperature upwards, it is also possible to use the present invention with downward temperature ramps. For example, when the temperature is lowered rapidly (e.g., at 100° C./min) down through the melting point of a crystalline polymer (e.g., nylon 11), the change in the phase signal observed at solidification is much less pronounced than the change in the phase signal obtained when temperature is lowered at, e.g., 15° C./min. This may indicate that locally the material has not fully returned to its crystalline from, but is still (possibly partially) amorphous. However, it is also possible that any mechanical loading effect depends upon the direction of the temperature increase or decrease.

Also, for a polymer at 20° C., on the basis of the rate at which the spatial resolution degrades with depth under the conditions required for thermal imaging, it can be estimated that a volume of a few cubic microns is probed. Of course, this volume will vary with both the temperature and the temperature ramping rate.

The foregoing disclosure of examples and embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

TABLE I

Characteristic Temperatures (degrees Centigrade):

| | glass transition | melting | thermal decomposition |
|---|---|---|---|
| polyethylene (high density) | −125 | 130 to 140 | 300 to 400 |
| poly(ethylene terephtalate) | 70 to 80 | 245 to 265 | 350 to 450 |
| polystyrene | 90 to 110 | | 325–400 |
| poly(methyl methacrylate) | 85 to 105 | | 240 to 350 |

TABLE I-continued

Characteristic Temperatures (degrees Centigrade):

|  | glass transition | melting | thermal decomposition |
|---|---|---|---|
| poly(vinyl chloride) | 65 to 85 | | |
| poly(phenylene oxide) | 210 to 225 | | |
| polycaprolactone | | 60 to 80 | 275 to 400 |
| poly(vinylidene floride) | −30 to −20 | 155 to 185 | 420 to 600 |
| poly(ethylene oxide) | −65 | 60 to 70 | |
| polybutadiene | −95 | | |
| poly(ethyl methacrylate) | 60 to 90 | | |
| nylon 11 | | 190 to 200 | |
| nylon 6 | 40 to 60 | 210 to 220 | 350 to 450 |
| nylon 6/10 | 44 to 55 | 215 to 220 | 400 to 450 |
| nylon 6/6 | 50 to 60 | 240 to 265 | |

TABLE II

Some thermophysical properties of the materials involved.

|  | Specific heat capacity ($J\ kg^{-1}\ K^{-1}$) | Thermal conductivity ($J\ s^{-1}m^{-1}K^{-1}$) | Thermal diffusivity ($\times 10^{-6}\ m^2 s^{-1}$) |
|---|---|---|---|
| Polystyrene | 1210 | 0.142 | 0.11 |
| Copper | 385 | 401 | 116 |
| Air | 1003 | 2.38 × 10 | 18.4 |

What is claimed is:

1. A method for performing localized thermal analysis experiments, comprising the steps of:
   (a) placing a sample on a stage;
   (b) exposing a particular location on the surface of said sample to a temperature generated in accordance with a temperature program having a constant component and an oscillatory component; and
   (c) measuring a physical parameter indicative of a thermal property of said sample at said particular location; and
   (d) recording a result of said measuring step (c).

2. The method as recited in claim 1, wherein step (b) comprises the steps of:
   (1) selecting an underlying heating rate to generate a temperature ramp as said constant component;
   (2) selecting a modulating function as said oscillatory component;
   (3) modulating said temperature ramp with said modulating function to generate said temperature program; and
   (4) generating said temperature in accordance with said temperature program.

3. The method as recited in claim 2, wherein step (2) comprises the step of selecting a modulation amplitude and a modulation frequency.

4. The method as recited in claim 3, wherein step (2) comprises the step of determining said modulation frequency and said modulation amplitude from said temperature program.

5. The method as recited in claim 3, wherein step (2) comprises the steps of:
   (i) digitizing said temperature to generate a digitized temperature; and
   (ii) determining said modulation frequency and said modulation amplitude from said digitized temperature.

6. The method as recited in claim 2, wherein step (2) comprises the step of selecting a repeating unit and a number of repetitions for said repeating unit.

7. The method as recited in claim 2, wherein step (1) comprises the step of selecting said underlying heating rate by averaging over a period of said modulation function.

8. The method as recited in claim 2, wherein said function is a sinusoid.

9. The method as recited in claim 1, further comprising the step of repeating steps (a)–(d) at a plurality of particular locations on the surface of said sample to thereby determine thermal properties of the sample at each of said plurality of particular locations.

10. The method as recited in claim 1, further comprising the step of separating the dependence of said physical parameter on said temperature into component parts.

11. The method as recited in claim 10, wherein said component parts comprises a reversing component and a non-reversing component.

12. The method as recited in claim 1, wherein said physical parameter is heat flow.

13. The method as recited in claim 1, wherein said stage is an X-Y stage.

14. An apparatus for performing localized thermal analysis experiments, comprising:
   a sample holder in which to place a sample;
   means for generating a temperature program by using a temperature program having a constant component and an oscillatory component;
   a sample probe to apply a temperature in accordance with said temperature program to said sample at a particular location on the surface of said sample;
   a reference probe to apply the temperature to a reference;
   monitoring means for monitoring a physical parameter indicative of a thermal property of said sample at said particular location; and
   recording means for recording a signal representative of said physical parameter at said particular location.

15. The apparatus as recited in claim 14, further comprising:
   means for applying said temperature to a plurality of locations on the surface of said sample by scanning said sample probe to each of said plurality of locations;
   means for monitoring said physical parameter at each of said plurality of locations; and
   means for recording a signal representative of said physical parameter at each of said plurality of locations.

16. The apparatus as recited in claim 14, wherein said physical parameter is a differential heat flow measured between said sample and reference probes.

17. The apparatus as recited in claim 14, wherein said reference probe is not in contact with any sample.

18. The apparatus as recited in claim 14, wherein said monitoring means comprising a lock-in-amplifier to monitor a phase and amplitude of said physical parameter corresponding to said time-varying component.

19. A method for sub-surface imaging of a sample using scanning thermal microscopy, comprising the steps of:
   (a) heating a location on a surface of a sample with a variable temperature having a frequency, using a localized heating element;
   (b) detecting an amount of heat flow at said location from said heating element to said sample;
   (c) developing contrast at a point in a sub-surface image map of the sample corresponding to said location, said contrast determined in accordance with said amount of heat flow.

20. The method as recited in claim 19, comprising the step of choosing said frequency according to a desired imaging depth below the surface of the sample.

21. The method as recited in claim 19, further comprising the steps of:

(d) scanning the heating element for a plurality of locations over the surface of the sample; and (e) performing steps (a)–(c) at each of said plurality of locations.

22. The method as recited in claim 21, wherein the heating element is a resistive probe, further comprising the steps of:

(f) maintaining a predetermined constant voltage having an underlying DC voltage and a modulated voltage across said resistive probe;

(g) measuring the variation of the voltage across said probe as said probe scans over said plurality of locations; and (h) determining said contrast in accordance with the phase or amplitude of the modulated voltage.

23. The method as recited in claim 22 where said resistive probe forms one leg of a wheatstone bridge, further comprising the step of:

(i) setting a balance for said bridge, wherein step (f) comprises the step of maintaining said balance in said bridge, and step (h) comprises the step of monitoring the modulated voltage across the bridge using a lock-in amplifier; and (j) determining a phase and an amplitude of the modulated signal using said lock-in amplifier to generate a contrast at each of said plurality of locations.

24. An apparatus for performing sub-surface imaging of a sample, comprising:

a stage on which to place the sample;

a heating source to heat a particular location of said sample, wherein said heating source exposes said particular location to a temperature that has an oscillatory component corresponding to a depth below said surface at which to create an image of said sample;

a sensor to detect a physical parameter indicative of the composition of the sample at said pre-determined depth;

means for developing contrast in said image at a location corresponding to said particular location of said sample; and a display device for displaying said image.

25. The apparatus as recited in claim 24, wherein said heating source comprises a thermal resistive probe.

26. The apparatus as recited in claim 24, wherein said oscillatory component is a sinusoid having a frequency that corresponds to said depth.

27. The apparatus as recited in claim 24, wherein said probe forms one leg of a Wheatstone bridge, further comprising a lock-in amplifier to monitor an amplitude and a phase associated with said oscillatory component, wherein said contrast is developed in accordance with said amplitude and phase.

* * * * *